United States Patent
Tang et al.

(10) Patent No.: US 12,239,982 B2
(45) Date of Patent: Mar. 4, 2025

(54) MICROFLUIDIC DEVICE AND DIAGNOSTIC METHODS FOR ALLERGY TESTING BASED ON DETECTION OF BASOPHIL ACTIVATION

(71) Applicants: Sindy K. Y. Tang, Palo Alto, CA (US); Kari C. Nadeau, Los Altos Hills, CA (US); Bryan J. Bunning, San Mateo, CA (US); Nicolas Castano, Stanford, CA (US); Fengjiao Lyu, Stanford, CA (US); Seth Cordts, Palo Alto, CA (US); The Board of Trustees of the Leland Stanford Junior University, Stanford, CA (US)

(72) Inventors: Sindy K. Y. Tang, Palo Alto, CA (US); Kari C. Nadeau, Los Altos Hills, CA (US); Bryan J. Bunning, San Mateo, CA (US); Nicolas Castano, Stanford, CA (US); Fengjiao Lyu, Stanford, CA (US); Seth Cordts, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 968 days.

(21) Appl. No.: 17/292,782

(22) PCT Filed: Nov. 13, 2019

(86) PCT No.: PCT/US2019/061288
§ 371 (c)(1),
(2) Date: May 11, 2021

(87) PCT Pub. No.: WO2020/102429
PCT Pub. Date: May 22, 2020

(65) Prior Publication Data
US 2021/0394183 A1    Dec. 23, 2021

Related U.S. Application Data

(60) Provisional application No. 62/888,884, filed on Aug. 19, 2019, provisional application No. 62/767,444, filed on Nov. 14, 2018.

(51) Int. Cl.
*B01L 1/00*    (2006.01)
*B01L 3/00*    (2006.01)
(Continued)

(52) U.S. Cl.
CPC .... *B01L 3/502761* (2013.01); *G01N 33/5047* (2013.01); *G01N 33/54366* (2013.01);
(Continued)

(58) Field of Classification Search
None
See application file for complete search history.

(56) References Cited

U.S. PATENT DOCUMENTS

| 8,563,258 B2 | 10/2013 | Sainte-Laudy et al. |
| 9,891,213 B2 | 2/2018 | Gernez et al. |

(Continued)

FOREIGN PATENT DOCUMENTS

| WO | 2017003380 A1 | 1/2017 |
| WO | 2018109146 A1 | 12/2017 |

(Continued)

OTHER PUBLICATIONS

Gao (2016) "Microfluidic sorting of bloods cells by negative selection," University of Cincinnati Thesis for master of science degree in electrical engineering, pp. 1-47.
(Continued)

*Primary Examiner* — Jyoti Nagpaul
(74) *Attorney, Agent, or Firm* — Jenny L. Buchbinder; Bozicevic, Field & Francis LLP

(57) ABSTRACT

Devices, methods, and kits are provided for allergy testing based on basophil activation in a blood sample. Suscepti-
(Continued)

bility of an individual to an allergic reaction to an allergen is detected by collecting a blood sample from the individual and assaying for activation of basophils in response to stimulation with an allergen. In particular, a microfluidic device is provided for automating the assay for detecting basophil activation as an indication of the susceptibility of an individual to an allergic reaction as well as kits containing such a device and diagnostic methods for using such a device for allergy testing. Additionally, such a microfluidic device can be adapted for multiplexed detection of allergic responses to multiple allergens by performing assays in parallel to detect the basophil responses to each allergen.

21 Claims, 22 Drawing Sheets

(51) Int. Cl.
  *G01N 33/50* (2006.01)
  *G01N 33/543* (2006.01)
  *G01N 33/569* (2006.01)
(52) U.S. Cl.
  CPC ............ *G01N 33/56972* (2013.01); *B01L 2200/0652* (2013.01); *B01L 2300/0819* (2013.01); *B01L 2300/088* (2013.01); *B01L 2300/0883* (2013.01); *G01N 2800/24* (2013.01)

(56) References Cited

U.S. PATENT DOCUMENTS

| | | |
|---|---|---|
| 10,114,012 B2 | 10/2018 | Gernez et al. |
| 2007/0099289 A1 | 5/2007 | Irimia et al. |
| 2009/0286300 A1 | 11/2009 | Le et al. |
| 2012/0083007 A1 | 4/2012 | Nadeau et al. |

FOREIGN PATENT DOCUMENTS

| | | |
|---|---|---|
| WO | 2018119401 A2 | 6/2018 |
| WO | WO2018199840 A1 * | 11/2018 |

OTHER PUBLICATIONS

Mukai et al. (2017) "A new fluorescent-avidin-based method for quantifying basophil activation in whole blood," J. Allergy Clin. Immunol. 140(4):1202-1206.e3.

* cited by examiner

MICROFLUIDIC DEVICE AND DIAGNOSTIC METHODS FOR ALLERGY TESTING BASED ON DETECTION OF BASOPHIL ACTIVATION

FEDERALLY SPONSORED RESEARCH AND DEVELOPMENT

This invention was made with Government support under contract AI149277 awarded by the National Institutes of Health. The Government has certain rights in the invention.

BACKGROUND

Allergies have reached epidemic proportions and have become a serious public health concern. Food allergies, in particular, are common with a prevalence of about 8% among U.S. children and costly with an estimated cost of $24.8 billion per year to the U.S. healthcare system. 40% of children with food allergies have experienced life-threatening allergic reactions. Emergency department visits and hospitalizations for allergies and allergen-induced anaphylaxis have also increased rapidly in the U.S. in the past decade.

Allergies develop as early as infancy and early childhood (<3 years of age) and can last a lifetime. However, allergy tests are not routinely performed as current tests lack sufficient predictive value, and/or often cause significant anxiety due to potential severe negative reactions by partaking of the test itself (e.g., oral food challenge). As such, allergies are often identified only after an adverse reaction that could be life-threatening.

Recently, a new allergy test using a novel blood biomarker based on the activation of basophils ("basophil activation test", or "BAT") has been developed. This test has been shown to have high accuracy in adults, children, and infants. However, the current test requires flow cytometers and experienced technicians to perform the analysis, both of which are not always accessible in clinical labs. Even for labs with flow cytometers, it takes at least 2 weeks for the results to be analyzed and returned to the patients. The 2 weeks of wait time could be the difference in risking another anaphylactic event as the patients still do not know what they are allergic to.

There is an urgent need for a more rapid, accessible standalone test for clinical diagnostics that can be conveniently used at a hospital, for example, in a doctor's office or the emergency room, so that patients of any age who experience adverse reactions can obtain results quickly to avoid repeated exposure to an offending allergen. A rapid diagnostic test would also be useful in monitoring the progress of treatment of patients undergoing food immunotherapy.

SUMMARY

Devices, methods, and kits are provided for allergy testing based on basophil activation in a blood sample. Susceptibility of an individual to an allergic reaction to an allergen is detected by collecting a blood sample from the individual and assaying for activation of basophils in response to stimulation with an allergen. An individual is identified as being allergic to a given allergen if the proportion of basophils activated by the allergen in the blood sample is greater than in the absence of the allergen or presence of a negative control. This type of allergy diagnostic test has the advantage over the skin prick test (SPT), commonly used for allergy screening, in that it performed ex vivo and does not trigger adverse allergic reactions (e.g., hives or anaphylaxis). In particular, devices are provided for automating the assay for detecting basophil activation as an indication of the susceptibility of an individual to an allergic reaction. Such devices will allow rapid, convenient diagnostic testing for allergies.

In one aspect, a microfluidic chip component is provided for automating detection of an allergic response to an allergen. In certain embodiments, the microfluidic chip component comprises: a) an allergen test chamber comprising an allergen; b) a first region for separating basophils from other blood cells by negative selection, wherein the first region comprises a plurality of immobilized binding agents capable of selectively binding to one or more cell surface markers on the other blood cells, wherein the cell surface markers are not expressed on basophils; c) a first fluidic channel, wherein the first fluidic channel connects the chamber comprising an allergen to the first region; d) a second region for capturing basophils by positive selection, wherein the second region comprises a plurality of immobilized binding agents capable of selectively binding to one or more cell surface markers on the basophils and capturing the basophils; e) a second fluidic channel, wherein the second fluidic channel connects the first region to the second region; and f) a means for detecting basophils activated by the allergen.

In certain embodiments, the microfluidic chip component further comprises a module for depleting red blood cells and platelets from the blood sample. This module may precede the first region for separating basophils from other blood cells by negative selection in the microfluidic chip component. This module may be designed to deplete red blood cells and platelets from the blood sample and separate them from the white blood cells by any known method. For example, the module may comprise a chamber comprising a lysis buffer for lysing the red blood cells. White blood cells can be separated by size or density by centrifugation, for example, in a spiral channel. For separation of white blood cells by density, a density gradient can be used. Alternatively, white blood cells can be separated using surface acoustic waves.

In some embodiments, the channels and chambers of the microfluidic chip component are comprised of poly(dimethylsiloxane) (PDMS) and glass. The microfluidic chip component may further comprise, for example, a chamber comprising a non-allergen negative control or a chamber comprising an anti-immunoglobulin E (IgE) antibody or other protein or chemical. The first and second regions may be contained, for example, in a chamber or fluidic channel within the microfluidic chip component.

In certain embodiments, the microfluidic chip component further comprises means for compartmentalizing discrete volumes of basophils, whole blood, or white blood cells into a plurality of separate microfluidic compartments.

In certain embodiments, the microfluidic chip component further comprises a plurality of compartments for separating discrete volumes of sample. For example, the plurality of compartments may comprise, without limitation, microfluidic wells, microfluidic liquid traps, or microfluidic channels, or a combination thereof. In some embodiments, the plurality of compartments comprises aqueous droplets, wherein each aqueous droplet is contained in oil or other immiscible fluid. In other embodiments, the plurality of compartments are plugs of fluid, wherein the plugs are separated by a hydrophobic liquid (e.g., oil), gas, or an immiscible fluid or substrate.

In certain embodiments wherein cells are compartmentalized, the microfluidic chip comprises a sensor or a multitude of sensors to measure fluorescence, colorimetric changes, chemiluminescent, or electrical impedance changes in individual compartments which contain cells. These sensors may be arranged in an array to simultaneously measure compartmentalized changes due to activation of basophils. Alternatively, sensors may be located at one position to interrogate compartments that are passed over the sensor.

In some embodiments, the sample obtained after removing red blood cells (e.g., from a DLD array) is compartmentalized along with reagents for detecting activated basophils, without enriching for basophils via negative and positive selection chambers (FIG. 14). The compartments containing an activated basophil have a higher fluorescence signal than a compartment containing non-basophils. In some embodiments, the method further comprises counting the number of compartments that have the higher fluorescence signal to determine the number of activated basophils.

In some embodiments, the whole blood sample is separated into compartments each containing one or more cells (FIG. 15). Each compartment is also injected with allergen to stimulate the basophils. After an incubation period, additional reagents can be injected into each compartment to detect activated basophils or mediators (e.g., histamine) released during basophil activation. In some embodiments, a fluorescent assay is used to detect the activated basophils or mediators (e.g., the assay reagent turns fluorescent only in the presence of the activated basophils or mediators). In some embodiments, the method further comprises counting the number of activated basophils by counting the number of fluorescent compartments.

In some embodiments, the compartments have a height between 10 and 500 micrometers, including any height within this range such as 10, 20, 30, 40, 50, 60, 70, 80, 90, 100, 120, 140, 160, 180, 200, 220, 240, 260, 280, 300, 320, 340, 360, 380, 400, 420, 440, 460, 480, and 500 micrometers.

In some embodiments, the choice of assay reagents and compartment size is determined such that whole blood does not interfere with the chemistry of the assay reagents nor the detection of a fluorescence signal due to the short optical path length of the compartments.

In certain embodiments, the plurality of immobilized binding agents capable of selectively binding to one or more cell surface markers on the basophils and capturing the basophils comprise at least one antibody selected from the group consisting of an anti-CD123 antibody, an anti-CD193 antibody, an anti-CD294 antibody, an anti-CCR3 antibody, an anti-CD192 antibody, and an anti-IgE antibody.

In certain embodiments, the plurality of immobilized binding agents capable of selectively binding to one or more cell surface markers on the other blood cells (i.e., non-basophils) that are not expressed on basophils comprise at least one antibody selected from the group consisting of an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody.

Antibodies may be immobilized on a solid support such as, but not limited to, a magnetic bead, a nonmagnetic bead, or a chamber wall or fluidic channel wall within the microfluidic chip component. In certain embodiments, the solid support comprises a herringbone structure or a pillar array. In some embodiments, the solid support is comprised of glass, metal, or poly(dimethylsiloxane) (PDMS). In certain embodiments, the solid support further comprises a coating. For example, the channels and/or chambers within the microfluidic chip component or other solid support may be coated with (3-aminopropyl) triethoxysilane (APTES) and/or bovine serum albumin (BSA). In one embodiment, the BSA is covalently attached to the APTES using a crosslinking agent (e.g., glutaraldehyde). In another embodiment, an agent capable of binding the antibody (e.g., protein A) is covalently attached to the BSA using a crosslinking agent (e.g., glutaraldehyde). In another embodiment, the immobilized antibody is adsorbed onto the solid support.

In certain embodiments, the allergen test chamber or the second region further comprises at least one detectably labeled binding agent capable of selectively binding to a basophil activation marker. Exemplary basophil activation markers include CD63 and CD203. In some embodiments, the detectably labeled binding agent comprises an antibody specific for a basophil activation marker covalently linked to a detectable label. Exemplary antibodies that may be used in the binding agent to detect basophil activation include an anti-CD203 antibody (detects early basophil activation), an anti-CD63 antibody (detects late basophil activation), and an anti-avidin antibody (detects basophil degranulation). In other embodiments, the detectably labeled binding agent comprises avidin covalently linked to a detectable label.

In certain embodiments, the detectable label is a fluorescent label, a chemiluminescent label, or an isotopic label.

In certain embodiments, the microfluidic chip component further comprises a flow-through microfluidic cytometer capable of measuring numbers of activated basophils, wherein the flow-through microfluidic cytometer is fluidically connected to the second region.

In certain embodiments, the microfluidic chip component further comprises a module for depleting red blood cells and platelets, wherein the module is fluidically connected to the chamber comprising the allergen. For example, the module for depleting red blood cells and platelets may comprise a red blood cell lysis module. Alternatively, the module for depleting red blood cells and platelets may comprise a pillared channel for depleting red blood cells and platelets by deterministic lateral displacement (DLD).

In certain embodiments, the microfluidic chip component comprises a fluorescence detector for detecting basophils activated by an allergen (i.e., detecting fluorescently labeled binding agent bound to activation markers on the activated basophils). For example, the fluorescence detector may be located at a position in the microfluidic chip component such that the fluorescence detector is capable of detecting fluorescence emitted from the captured activated basophils within the second region. Alternatively, activated basophils, after labeling with fluorescently labeled binding agents that bind to their activation markers, may be flowed to another site (i.e., detection site) in the microfluidic chip component for detection by a fluorescence detector positioned, for example, downstream of the second region in the microfluidic chip component.

In other embodiments, the microfluidic chip component comprises a sensor capable of detecting increases in electrochemical current associated with activation of the basophils by an allergen. For example, the sensor may comprise a microelectrode.

In certain embodiments, the microfluidic chip component further comprises electrical means for measuring changes in resistivity, impedance, or conductance associated with activation of the basophils by an allergen.

In certain embodiments, the microfluidic chip component further comprises a means for measuring serum IgE levels.

In certain embodiments, the microfluidic chip component further comprises a means for measuring basophil mediators (e.g., beta-hexosaminodase, histamine).

In another embodiment, the microfluidic chip component comprises: a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel; b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a wash buffer for removing unbound agents, wherein the chamber comprising the wash buffer for removing unbound binding agents is fluidically connected to the chamber for incubating activated basophils with detectably labeled binding agents, iii) a channel connecting the chamber for incubating activated basophils with detectably labeled binding agents and the chamber comprising the wash buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the wash buffer for removing unbound binding agents and v) a second waste outlet, wherein the second waste channel is fluidically connected to the second asymmetric serpentine inertial focusing channel; c) a third portion for lysing red blood cells comprising: i) a chamber comprising a lysis buffer, wherein the chamber comprising the lysis buffer is fluidically connected to the second asymmetric serpentine inertial focusing channel, ii) a chamber comprising a washing buffer, iii) a channel connecting the chamber comprising the lysis buffer and the chamber comprising the washing buffer, iv) a third asymmetric serpentine inertial focusing channel, wherein the third asymmetric serpentine inertial focusing channel is fluidically connected to the channel connecting the chamber comprising the lysis buffer and the chamber comprising the washing buffer, v) a third waste outlet, wherein the third waste outlet is fluidically connected to the third asymmetric serpentine inertial focusing channel; d) a fourth portion for sample fractionation comprising i) an inertial fractionation spiral and ii) a fourth waste outlet, wherein the fourth waste outlet is fluidically connected to the inertial fractionation spiral; and e) a fifth portion for capturing basophils comprising i) a basophil negative selection chamber, ii) a basophil positive selection chamber, wherein the basophil positive selection chamber is fluidically connected to the basophil negative selection chamber, iii) a chamber comprising a wash buffer, wherein the chamber comprising the wash buffer is fluidically connected to the basophil positive selection chamber, and iv) an exit channel, wherein the exit channel is fluidically connected to the basophil positive selection chamber. (See FIG. 7A.)

In another embodiment, a method of using such a microfluidic chip component (FIG. 7A) is provided. The method comprises: a) introducing the blood sample into the first inlet; b) introducing the allergen into the second inlet; c) flowing the blood sample and the allergen into the incubation channel, wherein basophils in the blood sample are exposed to the allergen for a time sufficient to allow activation of any basophil comprising an immunoglobulin E (IgE) specific for the allergen that is bound at an $F_c\varepsilon RI$ receptor; d) flowing the blood sample through the first asymmetric serpentine inertial focusing channel to the chamber for incubating activated basophils with detectably labeled binding agents, wherein contacting the activated basophils with said detectably labeled binding agents in said chamber results in said binding agents selectively binding to at least one activation marker on the activated basophils; e) removing the detectably labeled binding agents that have not bound to the activated basophils at said at least one activation marker by washing the basophils with the washing buffer; f) flowing the blood sample through the second asymmetric serpentine inertial focusing channel to the chamber for lysing red blood cells, wherein contacting the red blood cells in the blood sample with the lysis buffer lyses the red blood cells; g) flowing the blood sample through the third asymmetric serpentine inertial focusing channel to the inertial fractionation spiral, wherein red blood cells are separated from the basophils in the blood sample; h) depleting the blood sample of the red blood cells by expelling the red blood cells out of the fourth waste outlet; i) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils.

In another embodiment, the microfluidic chip component comprises: a) a first portion for sample fractionation comprising: i) a first inlet for loading a blood sample, ii) a second inlet for loading a running buffer, ii) a DLD array, wherein the DLD array is fluidically connected to the first inlet and the second inlet, and ii) a first waste outlet, wherein the first waste outlet is fluidically connected to the DLD array; b) a second portion for stimulating basophils comprising: i) a chamber comprising the allergen, wherein the chamber comprising the allergen is fluidically connected to the DLD array, ii) an incubation channel for stimulating the basophils in the blood sample with the allergen, wherein the incubation channel is fluidically connected to the chamber comprising the allergen, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel and vi) a second waste outlet, wherein the second waste outlet is fluidically connected to the first asymmetric serpentine inertial focusing channel; c) a third portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a third waste outlet, wherein the third waste outlet is fluidically connected to the second asymmetric serpentine inertial focusing channel; and d) a fourth portion for capturing basophils comprising i) a basophil negative selection chamber, ii) a basophil positive selection chamber, wherein the basophil positive selection chamber is fluidically connected to the basophil negative selection chamber, iii) a chamber comprising a wash buffer, wherein the chamber comprising the wash buffer is fluidically connected to the basophil positive selection chamber, and iv) an exit channel, wherein the exit channel is fluidically connected to the basophil positive selection chamber. (See FIG. 7B.)

In another embodiment, a method of using such a microfluidic chip component (FIG. 7B) is provided. The method comprises: a) introducing the blood sample into the first inlet; b) introducing the running buffer into the second inlet; c) flowing the blood sample through the DLD array, wherein the red blood cells are separated from the basophils in the blood sample; d) depleting the blood sample of the red blood cells by expelling the red blood cells out of the first waste outlet; e) flowing the blood sample into the chamber comprising the allergen; f) flowing the blood sample and the allergen into the incubation channel, wherein basophils in the blood sample are exposed to the allergen for a time sufficient to allow activation of any basophil comprising an immunoglobulin E (IgE) specific for the allergen that is bound at an $F_c\varepsilon RI$ receptor; g) flowing the blood sample through the first asymmetric serpentine inertial focusing channel to the chamber for incubating activated basophils with detectably labeled binding agents, wherein contacting the activated basophils with said detectably labeled binding agents in said chamber results in said binding agents selectively binding to at least one activation marker on the activated basophils; h) removing the detectably labeled binding agents that have not bound to the activated basophils at said at least one activation marker by washing the basophils with the washing buffer; i) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils.

In another embodiment, the microfluidic chip component comprises: a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel; b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel; c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells and platelets, wherein the third waste outlet is fluidically connected to the DLD array; and d) a fourth portion for capturing basophils comprising i) a basophil negative selection chamber, ii) a basophil positive selection chamber, wherein the basophil positive selection chamber is fluidically connected to the basophil negative selection chamber, iii) a chamber comprising a washing buffer, wherein the chamber comprising the washing buffer is fluidically connected to the basophil positive selection chamber, and iv) an exit channel, wherein the exit channel is fluidically connected to the basophil positive selection chamber. (See FIG. 7C.)

In another embodiment, a method of using such a microfluidic chip component (FIG. 7C) is provided. The method comprises: a) introducing the blood sample into the first inlet; b) introducing the allergen into the second inlet; c) flowing the blood sample and the allergen into the incubation channel, wherein basophils in the blood sample are exposed to the allergen for a time sufficient to allow activation of any basophil comprising an immunoglobulin E (IgE) specific for the allergen that is bound at an $F_c\varepsilon RI$ receptor; d) flowing the blood sample through the first asymmetric serpentine inertial focusing channel to the chamber for incubating activated basophils with detectably labeled binding agents, wherein contacting the activated basophils with said detectably labeled binding agents in said chamber results in said binding agents selectively binding to at least one activation marker on the activated basophils; e) removing the detectably labeled binding agents that have not bound to the activated basophils at said at least one activation marker by washing the basophils with the washing buffer; f) flowing the blood sample through the second asymmetric serpentine inertial focusing channel; g) flowing the blood sample through the DLD array, wherein the red blood cells are separated from the basophils in the blood sample; h) depleting the blood sample of the red blood cells by expelling the red blood cells out of the third waste outlet; i) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils.

In another embodiment, the microfluidic chip component comprises: a) a first portion for sample fractionation comprising: i) a first inlet for loading a blood sample, ii) a second inlet for loading a running buffer, ii) a DLD array, wherein the DLD array is fluidically connected to the first inlet and the second inlet, and ii) a first waste outlet for expelling red blood cells and platelets, wherein the first waste outlet is fluidically connected to the DLD array; and b) a second portion for capturing, stimulating, and labeling basophils comprising: i) a basophil negative selection chamber, ii) a basophil positive selection chamber, wherein the basophil positive selection chamber is fluidically connected to the basophil negative selection chamber, iii) a chamber comprising an allergen, wherein the chamber comprising the allergen is fluidically connected to the basophil positive selection chamber, and iv) a second waste outlet. (See FIG. 7D.)

In another embodiment, a method of using such a microfluidic chip component (FIG. 7D) is provided. The method comprises: a) introducing the blood sample into the first inlet; b) introducing the running buffer into the second inlet; c) flowing the blood sample through the DLD array, wherein the red blood cells are separated from the basophils in the blood sample; d) depleting the blood sample of the red blood cells by expelling the red blood cells out of the first waste outlet; e) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; f) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils; g) flowing the blood sample into the chamber comprising the allergen, wherein basophils in the blood sample are exposed to the allergen for a time sufficient to allow activation of any basophil comprising an immunoglobulin E (IgE) specific for the allergen that is bound at an $F_c\varepsilon RI$ receptor; h) adding detectably labeled binding agents that selectively binding to at least one activation marker on the activated basophils to the chamber comprising the allergen and the activated basophils; and i) removing the detectably labeled binding agents that have not bound to the activated basophils at said at least one activation marker by washing the basophils with the washing buffer.

In another embodiment, a microfluidic chip component is provided, the microfluidic chip component comprising: a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel; b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel; c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells, wherein the third waste outlet is fluidically connected to the DLD array; and d) a fourth portion for compartmentalizing the DLD array product into discrete volumes, wherein the fourth portion comprises a plurality of compartments, said compartments comprising fluidic or solid state chambers to contain cells.

In another embodiment, a microfluidic chip component is provided, the microfluidic chip component comprising: a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel; b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel; c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells, wherein the third waste outlet is fluidically connected to the DLD array; and d) a fourth portion for basophil isolation comprising: i) an incubation chamber for binding antibodies specific for non-basophils to non-basophils, ii) a flow channel for removing the non-basophils such that a basophil isolation product exits the flow channel; and e) a fifth portion for compartmentalizing the basophil isolation product into discrete volumes, wherein the fifth portion comprises a plurality of compartments, said compartments comprising fluidic or solid state chambers to contain cells.

In another embodiment, a microfluidic chip component is provided, the microfluidic chip component comprising: a) a first portion for compartmentalizing whole blood into discrete volumes, wherein the first portion comprises a plurality of compartments, said compartments comprising fluidic or solid state chambers to contain cells; b) a second portion for stimulating whole blood comprising: i) an inlet for loading an allergen, iii) an incubation channel for stimulating the basophils in the blood sample with the allergen, wherein the compartments of a) and the allergen inlet are fluidically connected to the incubation channel; c) a third portion for adding reagents to compartments containing activated basophils comprising: i) an inlet for adding reagents to detect activated basophils, ii) an incubation channel, wherein the compartments and the inlet for adding reagents to detect activated basophils are fluidically connected to the incubation channel; and d) a fourth portion for detecting a measurable signal for the activated basophils that are detected by the reagents.

In another aspect, a microfluidic device for detecting an allergic response to an allergen is provided comprising at least one microfluidic chip component described herein.

In another aspect, a method of using a microfluidic device described herein is provided. In certain embodiments, the method comprises: a) introducing a blood sample into the allergen test chamber comprising the allergen; b) contacting basophils in the blood sample with the allergen for a time sufficient to allow activation of any basophil comprising an immunoglobulin E (IgE) specific for the allergen that is bound at an $F_c\epsilon RI$ receptor; c) flowing the blood sample through the first fluidic channel to the first region for separating basophils from other blood cells by negative selection, wherein the blood cells other than the basophils are captured by contacting the blood cells with the plurality of immobilized binding agents in the first region; d) flowing the blood sample through the second fluidic channel to the second region for capturing basophils by positive selection, wherein the basophils are captured by contacting the basophils with the plurality of immobilized binding agents in the second region; and e) detecting the basophils activated by the allergen.

In certain embodiments, the basophils activated by the allergen are contacted with at least one detectably labeled binding agent capable of selectively binding to a basophil activation marker. Any unbound detectably labeled binding agent may be removed (e.g., by rinsing) before detecting the detectably labeled binding agent that is bound to the activation marker (e.g., CD63 or CD203) on basophils activated by the allergen.

In certain embodiments, the activated basophils are detected using an immunoassay such as, for example, including without limitation an enzyme-linked immunosorbent assay (ELISA), a radioimmunoassay (RIA), or an immunofluorescent assay (IFA).

In certain embodiments, the activated basophils are detected by measuring changes in resistivity, impedance, or conductance associated with activation of the basophils by the allergen.

In certain embodiments, the activated basophils are detected by detecting histamine secreted by activated basophils.

For embodiments of the microfluidic device comprising a flow-through microfluidic cytometer, as described herein, the method may further comprise counting the number of basophils activated by the allergen by flowing the activated basophils through the microfluidic cytometer.

Additionally, microfluidic devices described herein can be adapted for multiplexed detection of allergic responses to multiple allergens by performing assays in parallel to detect basophil responses to each allergen. For example, the microfluidic device may comprise multiple chambers, each comprising a different allergen that can be tested for its ability to activate basophils utilizing the devices and diagnostic methods described herein. In certain embodiments, the microfluidic device includes several parallel channels and chambers for separately analyzing activation of basophils from the same sample upon stimulation by the different allergens, and a series of detector or sensor units for detecting basophil activation in response to stimulation by the different allergens. Basophils from a single blood sample may be divided among the parallel channels and chambers to allow simultaneous analysis of the response to different allergens.

In another embodiment, a microfluidic allergy diagnostic system is provided comprising a plurality of any of the microfluidic chip components described herein, wherein in each microfluidic chip component, the allergen test chamber comprises a different allergen. In certain embodiments, the microfluidic allergy diagnostic system further comprises a common sample inlet fluidically connected to each of the allergen test chambers comprising the different allergens, wherein the blood sample is divided among the allergen test chambers before assaying for basophil activation. In other embodiments, the microfluidic allergy diagnostic system further comprises a separate sample inlet fluidically connected to each allergen test chamber, wherein blood samples (from the same or different individuals) can be added at each sample inlet.

In some embodiments a kit is provided comprising a microfluidic device for practicing the methods described herein. Kits may further comprise allergens for testing, detectably labeled binding agents for detecting activation of basophils (e.g., fluorescently labeled anti-CD63 antibodies, anti-CD203 antibodies, or anti-avidin antibodies, or fluorescently labeled avidin), basophil capture agents (e.g., an anti-CD123 antibody, an anti-CD193 antibody, an anti-CD294 antibody, an anti-CCR3 antibody, an anti-CD192 antibody, and an anti-IgE antibody), non-basophil capture agents (e.g., an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody), buffers, and the like for use in allergy testing and instructions for use.

BRIEF DESCRIPTION OF THE DRAWINGS

FIG. 7A shows a schematic of a microfluidic chip designed for carrying out the assay in the following order: 1) stimulating basophils (separate inlets for whole blood and allergen fluidically connected to an incubation channel for stimulating the basophils in the blood sample with the allergen, a chamber comprising a wash buffer, an asymmetric serpentine inertial focusing channel, and waste outlets); 2) labeling activated basophils (a chamber for incubating activated basophils with detectably labeled binding agents that selectively bind to at least one activation marker on the basophils, a chamber comprising a wash buffer for removing unbound agents, an asymmetric serpentine inertial focusing channel, and waste outlets); 3) lysing red blood cells (a chamber comprising lysis buffer, a chamber comprising a washing buffer, an asymmetric serpentine inertial focusing channel, and waste outlets); 4) sample fractionation (an inertial fractionation spiral and waste outlet); and 5) capturing basophils (a basophil negative selection chamber), a chamber comprising a wash buffer, a basophil positive selection chamber, and an exit channel). FIG. 7B shows a schematic of a microfluidic chip designed for carrying out the assay in the following order: 1) sample fractionation (inlets for blood sample and a running buffer, a DLD array for depletion of red blood cells and platelets, and a waste outlet for expelling red blood cells and platelets); 2) stimulating basophils (an incubation channel for stimulating the basophils in the blood sample with the allergen, chamber comprising a washing buffer, an asymmetric serpentine inertial focusing channel, and waste outlets); 3)) labeling activated basophils (a chamber for incubating activated basophils with detectably labeled binding agents that selectively bind to at least one activation marker on the basophils, a chamber comprising a wash buffer for removing unbound agents, an asymmetric serpentine inertial focusing channel, and waste outlets); and 4) capturing basophils (a basophil negative selection chamber, a basophil positive selection chamber, a chamber comprising a washing buffer, and an exit channel). FIG. 7C shows a schematic of a microfluidic chip designed for carrying out the assay in the following order: 1) stimulating basophils (separate inlets for whole blood and allergen fluidically connected to an incubation channel for stimulating the basophils in the blood sample with the allergen, chamber comprising a wash buffer, an asymmetric serpentine inertial focusing channel, and waste outlets); 2) labeling activated basophils (a chamber for incubating activated basophils with detectably labeled binding agents that selectively bind to at least one activation marker on the basophils, chamber comprising a washing buffer for removing unbound agents, an asymmetric serpentine inertial focusing channel, and waste outlets); 3) sample fractionation (a DLD array for depletion of red blood cells and platelets, a chamber comprising a running buffer, and a waste outlet for expelling red blood cells and platelets); and 4) capturing basophils (a basophil negative selection chamber, a basophil positive selection chamber, a chamber comprising wash buffer, and an exit channel). FIG. 7D shows a schematic of a microfluidic chip designed for carrying out the assay in the following order: 1) sample fractionation (separate inlets for a blood sample and a running buffer fluidically connected to a DLD array for depletion of red blood cells and platelets, and a waste outlet for expelling red blood cells and platelets); and 2) capturing, stimulating, and labeling basophils (a basophil negative selection chamber, a basophil positive selection chamber, a chamber for adding allergen for stimulation of basophils, detectably labeled binding agents that selectively bind to at least one activation marker on the basophils for detection of activated basophils followed by a wash buffer to remove unbound binding agents, and a waste outlet).

FIG. 11A shows time evolving standard curves. FIG. 11B shows time evolving signal of positive and negative controls of stimulated basophils. FIG. 11C shows a standard curve of fluorescent measurements at 60 minutes. FIG. 11D shows fluorescent measurements at 60 minutes of positive and negative controls of stimulated basophils.

DETAILED DESCRIPTION OF EMBODIMENTS

Figure 1:
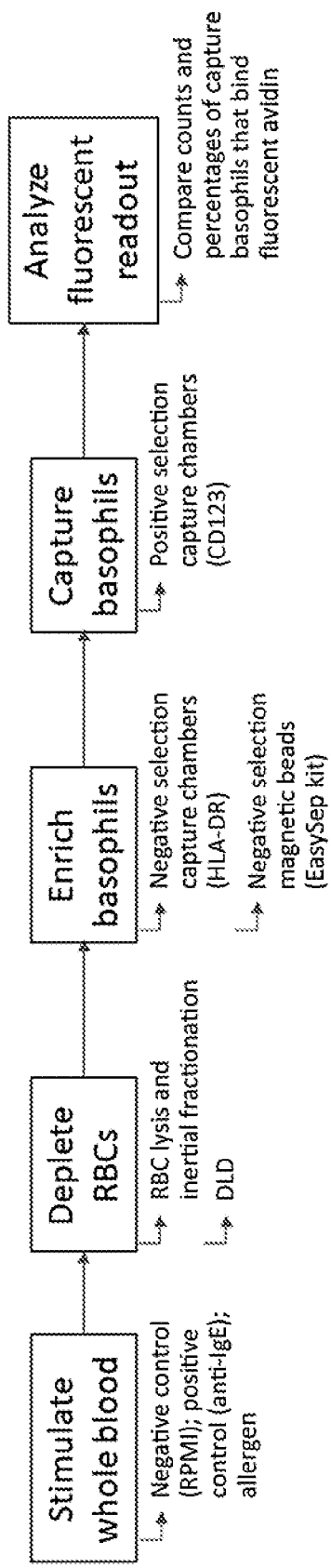
FIG. 1 shows the overall on-chip process flow.

Devices, methods, and kits are provided for allergy testing based on detection of basophil activation by allergens in a blood sample to determine the susceptibility of an individual to allergic responses to particular allergens.

Before the present devices, methods, and kits are described, it is to be understood that this invention is not limited to particular devices, methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a basophil" includes a plurality of such basophils and reference to "the allergen" includes reference to one or more allergens and equivalents thereof, e.g. allergens, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Obtaining and assaying a sample. The term "assaying" is used herein to include the physical steps of manipulating a biological sample to generate data related to the sample. As will be readily understood by one of ordinary skill in the art, a biological sample (e.g., blood sample containing basophils) must be "obtained" prior to assaying the sample (e.g., activation of basophils by an allergen). Thus, the term "assaying" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assaying may be relative or absolute. For example, "assaying" can be determining whether the basophil activation level is less than or "greater than or equal to" a particular threshold, (the threshold can be pre-determined or can be determined by assaying a control sample). On the other hand, "assaying to determine the basophil activation level" can mean determining a quantitative value (using any convenient metric) that represents the level of basophil activation. An individual is said to be allergic to a given allergen if the number of basophils activated by stimulation with the allergen is greater than the number of basophils activated by a negative control (i.e., control basophil activation test in absence of allergen or in presence of a non-allergenic control substance).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with an allergy, allergic inflammation, anaphylaxis, etc.) as well as those in which prevention is desired (e.g., those suspected of having an allergy, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

The term "allergy" is meant to encompass any allergic reaction resulting in activation of basophils or allergen-induced inflammation, such as caused by any ingested or inhaled allergen, occupational allergen, environmental allergen, drug, or any other substance that triggers a harmful immune reaction resulting in activation of basophils.

The terms "specific binding," "specifically binds," and the like, refer to non-covalent or covalent preferential binding to a molecule relative to other molecules or moieties in a solution or reaction mixture (e.g., an antibody specifically binds to a particular polypeptide (e.g., cell surface marker or allergen) or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-19}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Examples of binding pairs include antibody-antigen, IgE-allergen, and protein A-antibody binding pairs, and the like. Suitable specific binding members include agents that specifically bind to surface markers on activated basophils (e.g., an anti-CD63 antibody, an anti-CD203 antibody, or avidin), basophil capture agents that bind to surface markers on basophils (e.g., an anti-CD123 antibody, an anti-CD193 antibody, an anti-CD294 antibody, an anti-CCR3 antibody, an anti-CD192 antibody, and an anti-IgE antibody), and non-basophil capture agents that bind to surface markers on blood cells other than basophils (e.g., an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

"Providing an analysis" is used herein to refer to the delivery of an oral or written analysis (i.e., a document, a report, etc.). A written analysis can be a printed or electronic document. A suitable analysis (e.g., an oral or written report) provides any or all of the following information: identifying information of the subject (name, age, etc.), a description of what type of biological sample(s) was used and/or how it was used, the technique used to assay the sample, the results of the assay, the assessment as to whether the individual is determined to be susceptible to an allergic reaction to an allergen, a recommendation to continue or alter therapy, a recommended strategy for additional therapy, etc. The report can be in any format including, but not limited to printed information on a suitable medium or substrate (e.g., paper); or electronic format. If in electronic format, the report can be in any computer readable medium, e.g., diskette, compact disk (CD), flash drive, and the like, on which the information has been recorded. In addition, the report may be present as a website address which may be used via the internet to access the information at a remote site.

As used herein, the terms "detection agent", "diagnostic agent", and "detectable label" refer to a molecule or substance capable of detection, including, but not limited to, fluorescers, chemiluminescers, chromophores, bioluminescent proteins, enzymes, enzyme substrates, enzyme cofactors, enzyme inhibitors, isotopic labels, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-X-rhodamine (ROX), tetramethyl rhodamine (TAMRA), fluorescein isothiocyanate (FITC), dansyl, umbelliferone, dimethyl acridinium ester (DMAE), Texas red, luminol, and quantum dots, enzymes such as alkaline phosphatase (AP), beta-lactamase, chloramphenicol acetyltransferase (CAT), adenosine deaminase (ADA), aminoglycoside phosphotransferase (neor, G418r) dihydrofolate reductase (DHFR), hygromycin-B-phosphotransferase (HPH), thymidine kinase (TK), β-galactosidase (lacZ), and xanthine guanine phosphoribosyltransferase (XGPRT), beta-glucuronidase (gus), placental alkaline phosphatase (PLAP), and secreted embryonic alkaline phosphatase (SEAP). Enzyme tags are used with their cognate substrate. The terms also include chemiluminescent labels such as luminol, isoluminol, acridinium esters, and peroxyoxalate and bioluminescent proteins such as firefly luciferase, bacterial luciferase, Renilla luciferase, and aequorin. The terms also include isotopic labels, including radioactive and non-radioactive isotopes, such as, $^{3}H$, $^{2}H$, $^{120}I$, $^{123}I$, $^{124}I$, $^{125}I$, $^{131}I$, $^{35}S$, $^{11}C$, $^{13}C$, $^{14}C$, $^{32}P$, $^{15}N$, $^{13}N$, $^{110}In$, $^{111}In$, $^{177}Lu$, $^{18}F$, $^{52}Fe$, $^{62}Cu$, $^{64}Cu$, $^{67}Cu$, $^{67}Ga$, $^{68}Ga$, $^{86}Y$, $^{90}Y$, $^{89}Zr$, $^{94}mTc$, $^{94}Tc$, $^{99}mTc$, $^{154}Gd$, $^{155}Gd$, $^{156}Gd$, $^{157}Gd$, $^{158}Gd$, $^{15}O$, $^{186}Re$, $^{188}Re$, $^{51}M$, $^{52}Mn$, $^{55}Co$, $^{72}As$, $^{75}Br$, $^{76}Br$, $^{82m}Rb$, and $^{83}Sr$. The terms also include color-coded microspheres of known fluorescent light intensities (see e.g., microspheres with xMAP technology produced by Luminex (Austin, TX); microspheres containing quantum dot nanocrystals, for example, containing different ratios and combinations of quantum dot colors (e.g., Qdot nanocrystals produced by Life Technologies (Carlsbad, CA); glass coated metal nanoparticles (see e.g., SERS nanotags produced by Nanoplex Technologies, Inc. (Mountain View, CA); barcode materials (see e.g., sub-micron sized striped metallic rods such as Nanobarcodes produced by Nanoplex Technologies, Inc.), encoded microparticles with colored bar codes (see e.g., CellCard produced by Vitra Bioscience, vitrabio.com), glass microparticles with digital holographic code images (see e.g., CyVera microbeads produced by Illumina (San Diego, CA), near infrared (NIR) probes, and nanoshells. As with many of the standard procedures associated with the practice of the invention, skilled artisans will be aware of additional labels that can be used.

Microfluidic Devices and Diagnostic Methods of Using them for Allergy Testing

Devices, methods, and kits are provided for determining whether an individual is likely to have an allergic response to an allergen. Susceptibility of an individual to an allergic reaction to an allergen is detected by collecting a blood sample from the individual and assaying for activation of basophils in response to stimulation with the allergen. An individual is identified as being allergic to a given allergen if the proportion of basophils activated by the allergen in the blood sample is greater than in the absence of the allergen or presence of a negative control (i.e., non-allergenic substance). Higher numbers of activated basophils in response to exposure to an allergen correlate with increased severity of the expected allergic response to the allergen in the individual undergoing allergy testing.

In particular, a microfluidic device is provided for automating the assay for detecting basophil activation by an allergen as an indication of the susceptibility of an individual to an allergic reaction. The microfluidic device comprises a series of chambers, channels, valves, and microelectromechanical pumps that transport the blood sample comprising basophils from the entry point of the device to a sensor for detecting basophil activation, as well as out of the device after analysis. The channels, valves, and pumps are manufactured on a single substrate, which may be elastomeric or metallic in nature. Soft lithography techniques are typically used for an elastomeric substrate, whereas photolithography or electron beam lithography can be used for the patterning of metallic or semiconductor substrates. Microchannels can be fabricated, for example, from poly(dimethylsiloxane) (PDMS) using soft lithography. Inlets and outlets of the microchannels can be created using a biopsy puncher (see Examples).

Blood samples can be collected from a subject, for example, by venipuncture, finger prick, or heel prick. The concentration of basophils in whole blood is typically approximately $10^4$ to $10^5$ cells/ml, which is sufficient for analysis in a microfluidics device as described herein. Generally, blood samples are processed immediately or as soon as possible after they are obtained to avoid deterioration of the samples and loss of the capacity of basophils to be activated by stimulation with allergens. It will be understood by one of ordinary skill in the art that in some cases, it is convenient to wait until multiple samples (e.g., multiple blood samples each stimulated with a different test allergen) have been obtained prior to assaying the samples. Accordingly, in some cases an isolated biological sample (e.g., a blood sample stimulated with a test allergen) is stored until all appropriate samples have been obtained. One of ordinary skill in the art will understand how to appropriately store a variety of different types of biological samples and any convenient method of storage may be used (e.g., refrigeration, freezing) that is appropriate for the particular biological sample.

In certain embodiments, the volume of the blood sample loaded into a microfluidic device ranges from at least 5 µl, at least 10 µl, at least 25 µl, at least 50 µl, at least 100 µl, at least 250 µl, or at least 500 µl up to 1 ml, including any volume within this range, such as 5, 10, 20, 30, 40, 50, 60, 70, 80, 90, 100, 120, 140, 160, 180, 200, 225, 250, 300, 350, 400, 450, 500, 550, 600, 700, 750, 800, 850, 900, 950, or 1000 µl of blood. The number of basophils loaded into a microfluidic device is generally at least $10^3$, but may be greater, such as at least $10^4$, at least $10^5$, or at least $10^6$ basophils, etc.

The amount of allergen used to stimulate basophils may range from at least about 1 ng, at least about 10 ng, at least about 0.1 µg, at least about 1 µg, at least about 10 µg, or more in a single chamber. The specific amount can be selected based on the allergen in question.

The microfluidic devices involved in the processing of blood can be designed and operated such that expected shear stresses remain below or equal to physiological shear stresses in blood vessels. This ensures negligible artificial activation of basophils due to shear stresses. In some embodiments, the maximum allowable shear stress under a given channel geometry and flow rate is 40 dyn/cm². In some embodiments, microfluidic devices are verified to not artificially activate basophils by injecting whole blood into the device, collecting the blood at the outlet and running a conventional BAT protocol to check whether there is any unintended artificial activation of basophils.

A schematic of the overall microfluidic on-chip process flow is shown in FIG. 1. A blood sample comprising basophils is collected from a subject for allergy testing and introduced into the microfluidic device. The blood sample may be stimulated with a test allergen outside of the confines of the device or inside of the device by bringing the blood sample in contact with an allergen contained within a chamber or channel within the microfluidic device. In one embodiment, the microfluidic device contains a chamber comprising a candidate allergen for testing (i.e., an allergen test chamber). The basophils in the blood sample are introduced into the chamber and allowed to remain in contact with the allergen for a time sufficient to allow activation of any basophil comprising an immunoglobulin E (IgE) specific for the allergen, which is bound at an $F_c\varepsilon RI$ receptor on its cell surface. In certain embodiments, the blood sample is flowed through a fluidic channel to a region designed for separating basophils from other blood cells by negative selection. In certain embodiments, the blood cells other than the basophils are captured by contacting the blood cells with a plurality of immobilized binding agents in this region that selectively bind to one or more cell surface markers expressed on the other blood cells (i.e., non-basophils), which are not expressed on basophils. After basophil enrichment in this region by negative selection, the sample is flowed through a fluidic channel to a region for capturing basophils by positive selection. Here, the basophils are captured by contacting the basophils with a plurality of immobilized binding agents that selectively bind to one or more cell surface markers on the basophils and capture the basophils. Captured basophils that have been activated by stimulation with an allergen are then detected. In some embodiments, the basophils are contacted with an agent that labels the activated basophils to facilitate their detection. The ordering of the steps in this process may be varied in various ways. For example, the basophils may be captured before they are stimulated with the allergen, followed by labeling of the activated basophils for detection.

In one embodiment, the microfluidic device comprises at least one microfluidic chip component comprising: a chamber comprising an allergen for testing; a first region for separating basophils from other blood cells by negative selection, wherein the first region comprises a plurality of immobilized binding agents capable of selectively binding to one or more cell surface markers on the other blood cells (non-basophils), wherein the cell surface markers are not expressed on basophils; a first fluidic channel, wherein the first fluidic channel connects the chamber comprising an allergen to the first region; a second region for capturing basophils by positive selection, wherein the second region comprises a plurality of immobilized binding agents capable of selectively binding to one or more cell surface markers on the basophils and capturing the basophils; a second fluidic channel, wherein the second fluidic channel connects the first region to the second region; and a means for detecting basophils activated by the allergen.

In another embodiment, the microfluidic device further comprises one or more additional chambers for positive and/or negative controls for the assay. For example, the microfluidic device may comprise a chamber comprising a non-allergen negative control (e.g., RPMI media) or a chamber comprising a positive control (an anti-IgE antibody).

Figure 2:
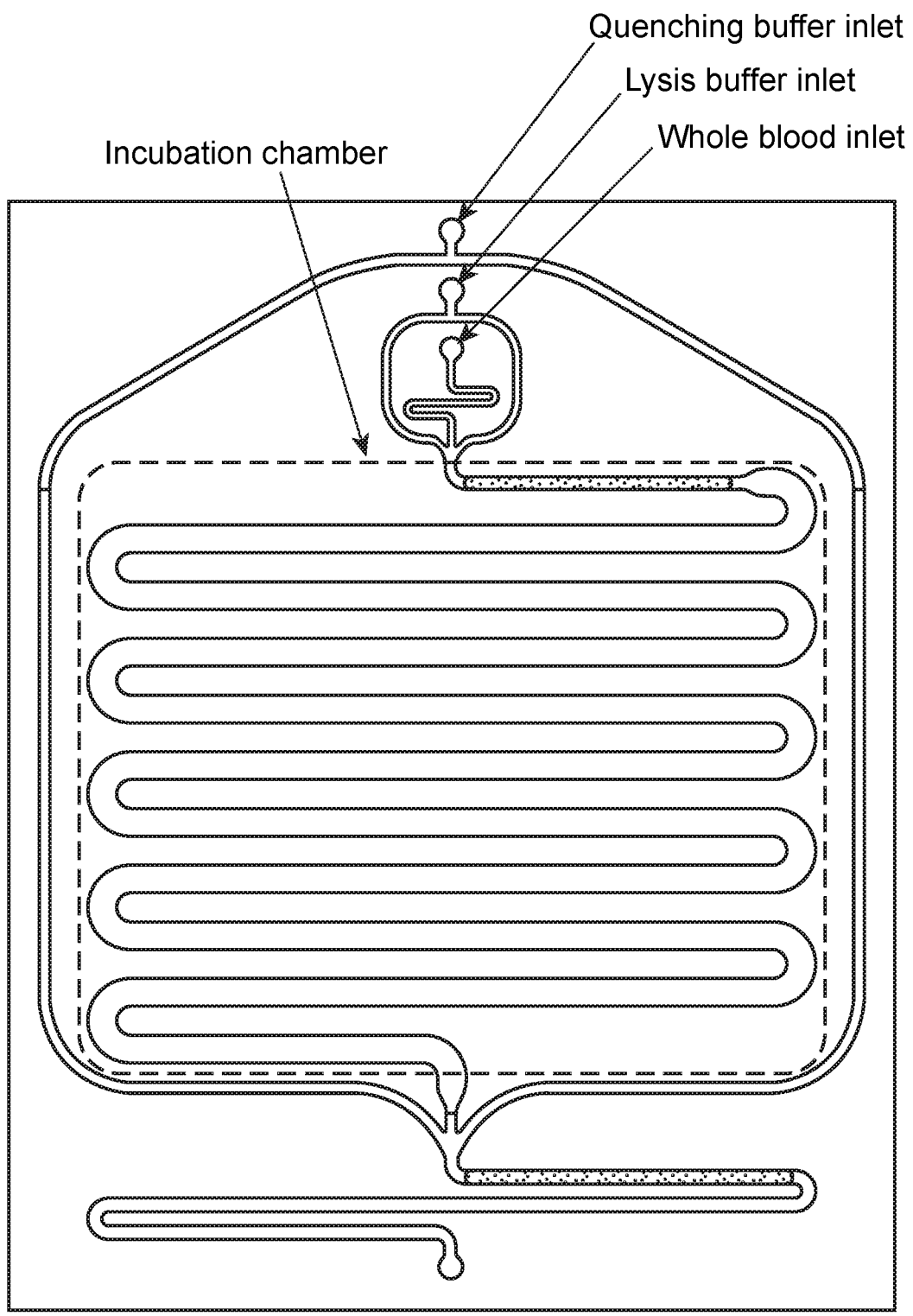
FIG. 2 shows a red blood cell lysis module.
Figure 3:
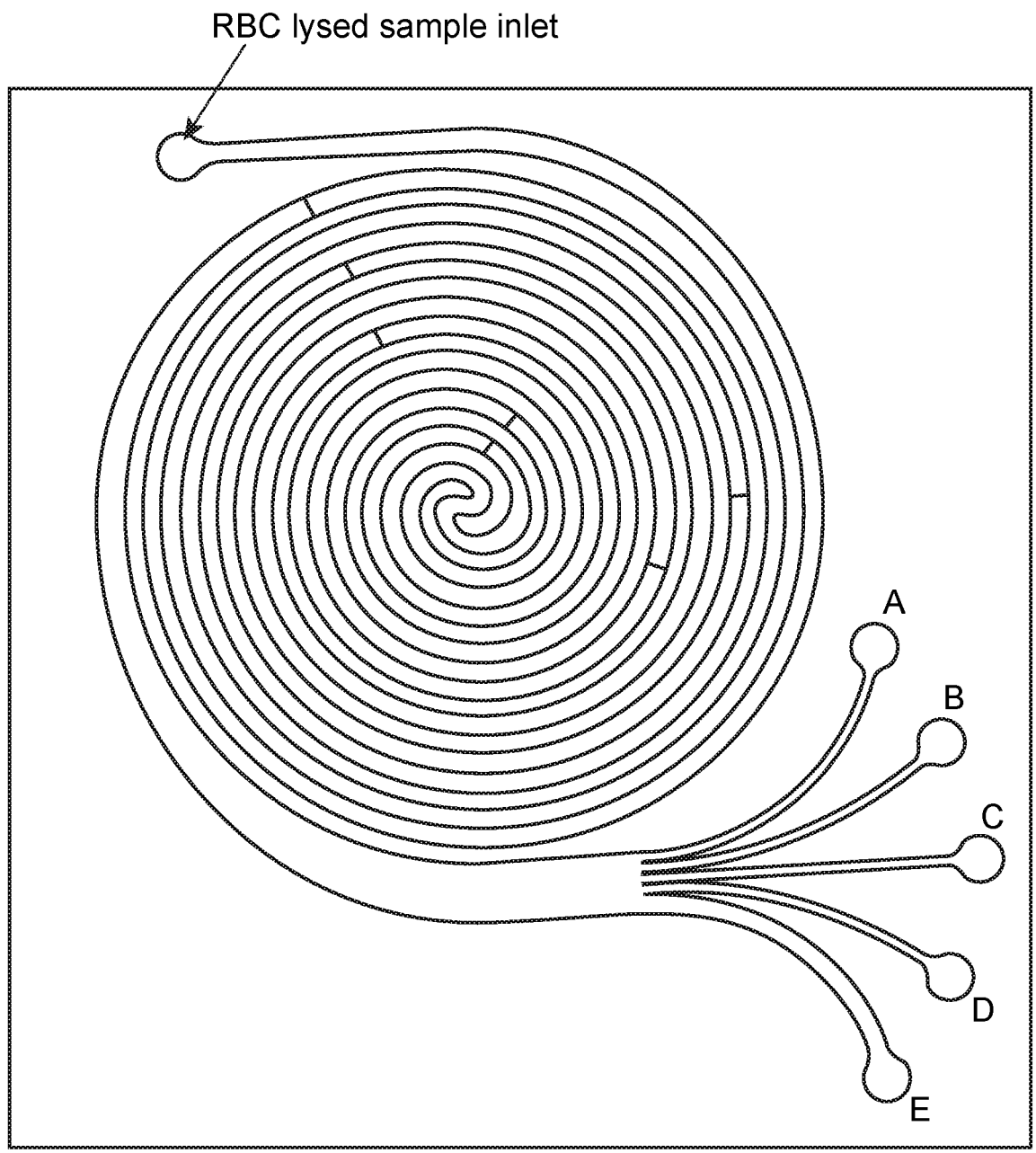
FIG. 3 shows an inertial fractionation spiral showing the outlet labels
Figure 4:
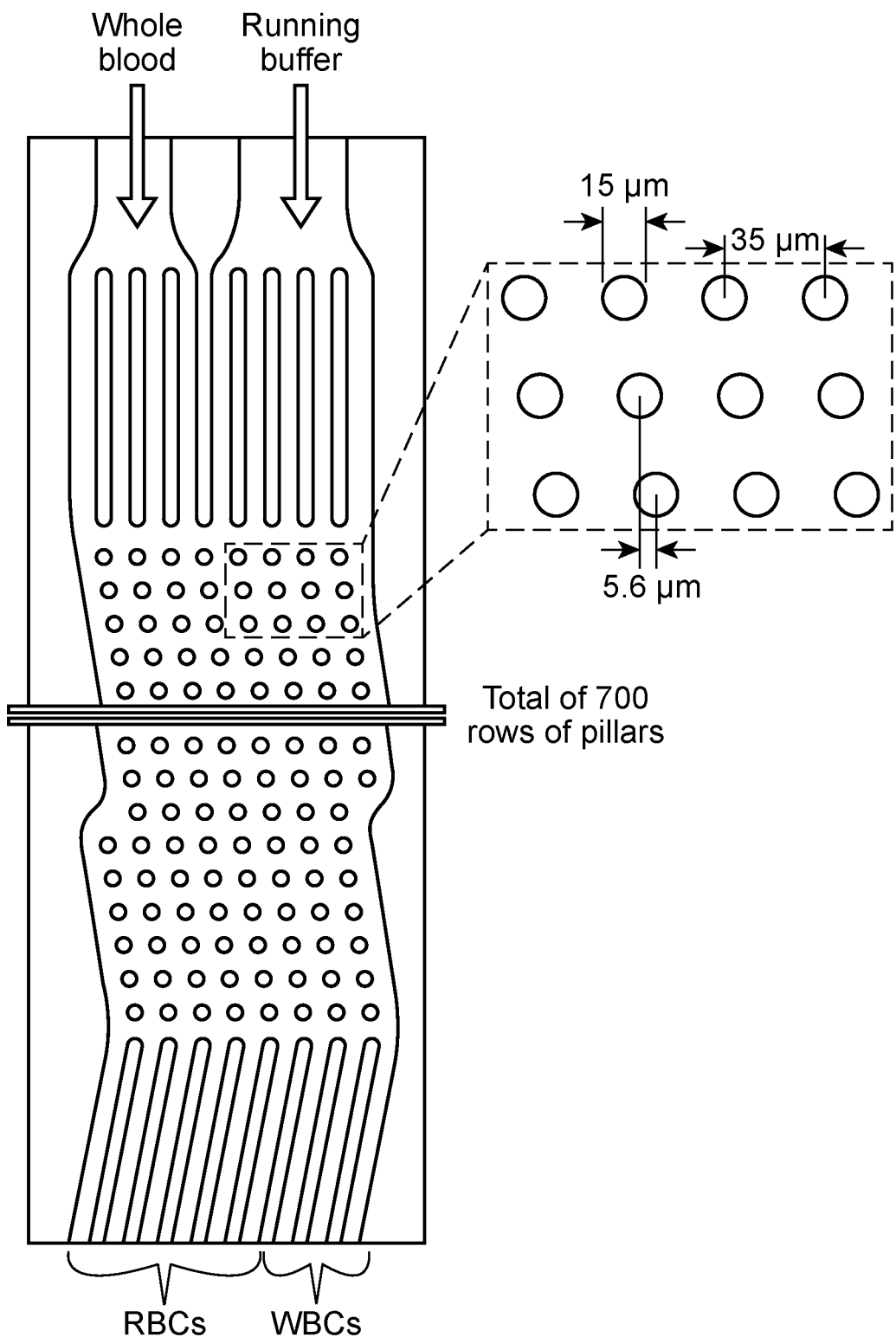
FIG. 4 shows a deterministic lateral displacement (DLD) array.

In certain embodiments, the microfluidic device further comprises a module for depleting red blood cells and platelets, wherein the module is fluidically connected to the chamber comprising the allergen. For example, the module for depleting red blood cells and platelets may comprise a red blood cell lysis module (FIGS. 2 and 3). The lysis method for use with the device should be chosen such that only the red blood cells are lysed while keeping the other leukocytes intact, including the basophils. Red blood cells can be lysed, for example, by osmotic shock using a solution containing ammonium chloride or saponin, which can be added to a chamber in the red blood cell lysis module. In certain embodiments, the red blood cell lysis module further comprises asymmetric serpentine channels to focus the blood sample after lysis of the red blood cells. The lysis buffer may be further diluted to avoid interference with downstream processing of the blood sample. In one embodiment, the microfluidic device further comprises an inertial fractionation spiral, which the white blood cells are passed through to separate them from the lysis solution. The white blood cells are then collected, now depleted of the red blood cells and platelets (FIG. 3). Alternatively, the module for depleting red blood cells and platelets may comprise a pillared channel for separating the red blood cells and platelets from the white blood cells by deterministic lateral displacement based on differences in their sizes (FIG. 4). White blood cells may also be separated from the red blood cells and platelets by size or density using centrifugation, for example, in a spiral channel (e.g., 9.5 mm in diameter, 10 loops, Dean number about 6.2). For separation of white blood cells by density, a density gradient can be used. Alternatively, white blood cells can be separated using surface acoustic waves.

The blood sample can be further enriched for basophils by flowing the sample through the first region, which separates basophils from other blood cells (i.e., non-basophils) by negative selection. In certain embodiments, the first region comprises a plurality of immobilized binding agents capable of selectively binding to one or more cell surface markers that are present on the non-basophils but not on the basophils in the blood sample. Such binding agents may comprise an antibody, aptamer, or ligand specific for a cell surface marker on non-basophils. In some embodiments, the binding agent comprises at least one antibody selected from the group consisting of an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody.

Next, the blood sample is flowed to the second region in the microfluidic device where the basophils are captured. In certain embodiments, the second region comprises a plurality of immobilized binding agents capable of selectively binding to one or more cell surface markers that are present on the basophils. Such binding agents may comprise an antibody, aptamer, or ligand specific for a cell surface marker on the basophils. In some embodiments, the binding agent comprises at least one antibody selected from the group consisting of an anti-CD123 antibody, an anti-CD193 antibody, an anti-CD294 antibody, an anti-CCR3 antibody, an anti-CD192 antibody, and an anti-IgE antibody.

In some embodiments, the binding agents specific for cellular markers, such as used in enriching and/or capturing basophils by negative or positive selection, respectively, are immobilized on a solid support. For example, binding agents may be attached to magnetic bead or nonmagnetic beads to separate cells from the mobile phase. Alternatively, binding agents can be attached to a chamber wall or fluidic channel wall within the microfluidic device. The solid support may be composed, for example, of glass, metal, or poly(dimethylsiloxane) (PDMS). In some embodiments, the microfluidic device comprises a herringbone structure or a pillar array in a channel or chamber of the microfluidic device where the binding agents are attached.

In certain embodiments, the solid support further comprises a coating to facilitate functionalization for attachment of the binding agents. Binding agents can be conjugated directly or indirectly to the coating. In one embodiment, the channels and/or chambers within the microfluidic device or other solid support (e.g., beads, slide, or plate) are coated with (3-aminopropyl) triethoxysilane (APTES). BSA can be covalently attached to the APTES using a crosslinking agent. In another embodiment, an agent capable of binding antibodies (e.g., protein A) is covalently attached to the substrate using a crosslinking agent for the purpose of immobilizing antibodies on the solid support (see, e.g., FIGS. 5 and 6).

Crosslinking agents that can be used include, but are not limited to, dimethyl suberimidate, N-hydroxysuccinimide, formaldehyde, and glutaraldehyde. In addition, carboxyl-reactive chemical groups such as diazomethane, diazoacetyl, and carbodiimide can be included for crosslinking carboxylic acids to primary amines. In particular, the carbodiimide compounds, 1-ethyl-3-(-3-dimethylaminopropyl) carbodiimide hydrochloride (EDC) and N',N'-dicyclohexyl carbodiimide (DCC) can be used for conjugation with carboxylic acids. In order to improve the efficiency of crosslinking reactions, N-hydroxysuccinimide (NHS) or a water-soluble analog (e.g., Sulfo-NHS) may be used in combination with a carbodiimide compound. The carbodiimide compound (e.g., EDC or DCC) couples NHS to carboxyl groups to form an NHS ester intermediate, which readily reacts with primary amines at physiological pH. In addition, ultraviolet light can be used for crosslinking proteins. For a description of various crosslinking agents and techniques, see, e.g., Wong and Jameson Chemistry of Protein and Nucleic Acid Cross-Linking and Conjugation (CRC Press, $2^{nd}$ edition, 2011), Hermanson Bioconjugate Techniques (Academic Press, $3^{rd}$ edition, 2013), herein incorporated by reference in their entireties.

In certain embodiments, crosslinking is performed using click chemistry. Crosslinking with click chemistry can be performed with suitable crosslinking agents comprising reactive azide or alkyne functional groups. See, e.g., Kolb et al., 2004, Angew Chem Int Ed 40:3004-31; Evans, 2007, Aust J Chem 60:384-95; Millward et al. (2013) Integr Biol (Camb) 5(1):87-95, Lallana et al. (2012) Pharm Res 29(1): 1-34, Gregoritza et al. (2015) Eur J Pharm Biopharm. 97(Pt B):438-453, Musumeci et al. (2015) Curr Med Chem. 22(17):2022-2050, McKay et al. (2014) Chem Biol 21(9): 1075-1101, Ulrich et al. (2014) Chemistry 20(1):34-41, Pasini (2013) Molecules 18(8):9512-9530, and Wangler et al. (2010) Curr Med Chem. 17(11):1092-1116; herein incorporated by reference in their entireties.

In particular, crosslinking can be performed using strain-promoted azide-alkyne cycloaddition (SPAAC) click chemistry, a Cu-free variation of click chemistry that is generally biocompatible with cells. SPAAC utilizes a substituted cyclooctyne having an internal alkyne in a strained ring system. Ring strain together with electron-withdrawing substituents in the cyclooctyne promote a [3+2] dipolar cycloaddition with an azide functional group. SPAAC can be used for bioconjugation and crosslinking by attaching azide and cyclooctyne moieties to molecules. For a description of SPAAC, see, e.g., Baskin et al. (2007) Proc Natl Acad Sci USA 104(43):16793-16797, Agard et al. (2006) ACS Chem. Biol. 1: 644-648, Codelli et al. (2008) J. Am. Chem. Soc. 130:11486-11493, Gordon et al. (2012) J. Am. Chem. Soc. 134:9199-9208, Jiang et al. (2015) Soft Matter 11(30):6029-6036, Jang et al. (2012) Bioconjug Chem. 23(11):2256-2261, Ornelas et al. (2010) J Am Chem Soc. 132(11):3923-3931; herein incorporated by reference in their entireties.

In certain embodiments, the basophils activated by a test allergen are detected by contacting them with at least one detectably labeled binding agent capable of selectively binding to a basophil activation marker. Such binding agents may comprise an antibody, aptamer, or ligand specific for a cell surface marker on the activated basophils. Exemplary basophil activation markers include CD63 and CD203. In some embodiments, the detectably labeled binding agent comprises an antibody specific for a basophil activation marker covalently linked to a detectable label. Exemplary antibodies that may be used in the binding agent to detect basophil activation include an anti-CD203 antibody (detects early basophil activation), an anti-CD63 antibody (detects late basophil activation), and an anti-avidin antibody (used in combination with avidin to detect basophil degranulation). In other embodiments, the detectably labeled binding agent comprises avidin covalently linked to a detectable label for detection of degranulation by activated basophils. Avidin stains negatively charged proteoglycans of the basophil granule matrix that become exposed upon degranulation. After binding of the binding agents to the activated basophils, any unbound binding agent may be removed before detection of the activated basophils, for example by rinsing the basophils.

The binding agents specific for cellular markers (e.g., antibodies, aptamers, or ligands), which are used in enriching and/or capturing basophils by negative or positive selection and/or labeling basophils activated by an allergen should be used in an amount sufficient to bind to the applicable blood cells. For example, the amount of a binding agent used will typically range from about 0.5 µg to about 50 µg, including any amount within this range, such as 0.5, 1, 2, 3, 4, 5, 6, 7, 8, 9, 10, 15, 20, 25, 30, 35, 40, 45, or 50 µg. The exact amount needed will vary and depend on the particular binding agent selected and its affinity for a particular cellular marker.

In certain embodiments, the microfluidic device comprises a fluorescence detector for detecting activated basophils having fluorescently labeled binding agents bound to them. The fluorescence detector may be located at a position in the microfluidic device such that the fluorescence detector is capable of detecting fluorescence emitted from the captured activated basophils within the second region. Alternatively, activated basophils, after labeling with fluorescently labeled binding agents that bind to their activation markers, may be flowed to another site (i.e., detection region) in the microfluidic site for detection by a fluorescence detector positioned, for example, downstream of the second region in the microfluidic device. For detection, the activated basophils are illuminated with an exterior light source at a fluorescence excitation wavelength of the fluorescent label on the binding agents. Excitation light sources that can be used include arc lamps and lasers, laser diodes and other light emitting diode sources, and both single and multiple photon excitation sources.

In some embodiments, basophil activation is measured using an immunoassay with an antibody specific for a basophil activation marker. Any suitable immunoassay technique known in the art may be used including, without limitation, an enzyme-linked immunosorbent assay (ELISA), a radioimmunoassay (RIA), or an immunofluorescent assay (IFA). For example, basophil activation can be measured using an ELISA with basophil activation markers (e.g., CD203c or CD63) conjugated to, e.g., horseradish peroxidase (HRP), alkaline phosphatase (AP), or other enzyme that enables the production of a detectable signal with a chromogenic substrate. Examples of ELISA enzyme-substrate combinations that can be used include without limitation, HRP with chromogenic substrates such as but not limited to, AmplexRed or QuantaRed, which produce fluorescent products (resorufin) that can be detected, o-phenylenediamine dihydrochloride (OPD), which produces an orange-brown product that can be detected spectrophotometrically, 2,2'-azinobis [3-ethylbenzothiazoline-6-sulfonic acid]-diammonium salt (ABTS) which produces a green product that can be detected spectrophotometrically; and AP with chromogenic substrates such as p-nitrophenyl phosphate (PNPP), which produces a yellow product that can be detected spectrophotometrically, and 5-bromo-4-chloro-3-indolyl phosphate (BCIP), which produces a blue/purple product that can be detected spectrophotometrically. Activation of basophils results in more intense signals for a basophil-specific marker that increases expression during activation. As CD203c is present on non-activated basophils and is upregulated upon activation, the CD203c marker provides a means for a single-marker readout for detecting basophils, both activated and non-activated, within a compartment of white blood cells.

In some embodiments, a coupled enzyme reaction may be used to improve specificity in detecting activated basophils. For example, histamine, a basophil-derived mediator indicative of activation, can be detected using an enzymatic reaction catalyzed by diamine oxidase, which produces $H_2O_2$ as a byproduct. $H_2O_2$ produced by this reaction can be detected using a peroxidase with a chromogenic substrate as described above (e.g., detecting oxidation of AmplexRed to resorufin). Since histamine is a mediator released by basophils after stimulation, and CD203c surface markers are upregulated by basophils upon stimulation, a coupled reaction of the histamine assay and CD203c conjugated to peroxidase will detect cells having high expression of CD203c and histamine secretion. For example, cells that express high levels of CD203c and secrete histamine are identified as activated basophils; cells that are low in histamine or low in CD203c are identified as non-basophils or non-activated basophils; cells that are high in histamine and low in CD203c are identified as non-basophils or non-activated basophils; and cells that are low in histamine and high in CD203c are identified as non-basophils or non-activated basophils. This increases specificity by filtering out cells that might have upregulated CD203c which are not activated basophils, while also eliminating cells that secrete histamine and are not activated basophils.

In some embodiments, an optical method is used to detect basophil activation that utilizes silver reduction chemistry. For example, silver reduction chemistry can be used in combination with an ELISA-based method with a secondary antibody that is conjugated to gold nanoparticles. The secondary antibodies bind to primary antibodies used for labeling a specified analyte (e.g., basophil activation marker or secretory product). In a solution of silver nitrate and hydroquinone, gold colloids catalyze the reduction of silver ions to silver atoms to form a silver film, which has an optical density that correlates with the analyte concentration. In this assay, the analyte may be a cell surface marker such as CD203c, or a mediator secreted by basophils or other white blood cells, such as histamine.

In other embodiments, the microfluidic device comprises a sensor capable of detecting increases in electrochemical current associated with activation of the basophils by an allergen. For example, the sensor may comprise a microelectrode. During degranulation of basophils due to stimulation by an allergen, negatively charged proteoglycans are exposed on the surface of the cell membrane. This alters the surface charge and membrane capacitance of the cell. In some embodiments, basophil activation is measured by an electrical method, such as by measuring impedance to detect the change in surface charge and/or membrane capacitance. Basophils flowing past a neighboring electrode will cause a change in impedance measured between the electrodes. Activated basophils are identified by a different impedance change compared with non-activated basophils.

In some embodiments, basophil activation is monitored over time with a series of measurements. As some embodiments rely on enzymatic reactions, time-varying measurements of signals can be used in monitoring basophil activation. In addition to end-point readouts, i.e. after basophils have been labeled with a detectable label (fluorescent or chemiluminescent label), time dependent measurements indicate rates of enzymatic reactions and improve detection of activated basophils. Furthermore, time series measurements of basophil impedance can also provide correlations to patient-specific rates of allergic reactions.

In some embodiments, the microfluidic device further comprises a flow-through microfluidic cytometer, for counting the number of basophils activated by an allergen. After enrichment of the basophils by negative selection and capture by positive selection, the basophils that have been activated by stimulation with an allergen may be flowed through a microfluidic cytometer. For a review of microfluidic cytometers and their use in microfluidic devices, see, e.g., Ehrlich et al. (2011) Methods Cell Biol. 102:49-75, Piyasena et al. (2014) Lab Chip 14(6):1044-1059, and Gong et al. (2018) "New advances in microfluidic flow cytometry" Electrophoresis [Epub ahead of print]; herein incorporated by reference.

In certain embodiments, the microfluidic device further comprises a means for measuring serum IgE levels. IgE levels can be measured by methods well known in the art, for example, with a microfluidic immunofluorescence assay, radioimmunoassay, enzyme-linked immunosorbent assay (ELISA), or ImmunoCAP assay. See, e.g., Proczek et al. (2012) Anal Bioanal Chem. 402(8):2645-2653, Shyur et al. (2010) Pediatr Allergy Immunol. 21(4 Pt 1):623-633, and Ewan et al. (1990) Allergy 45(1):22-29; herein incorporated by reference.

In certain embodiments, the microfluidic device further comprises a means for measuring basophil mediators. Mediators produced by basophils in response to activation by allergens include, but are not limited to, histamine, heparin, lipid mediators such as LTC4, LTD4, and LTE4, cytokines/chemokines such as IL-4, IL-13, GM-CSF, and IL-4, and enzymes, β-hexosaminidase and granzyme B.

Figure 8:
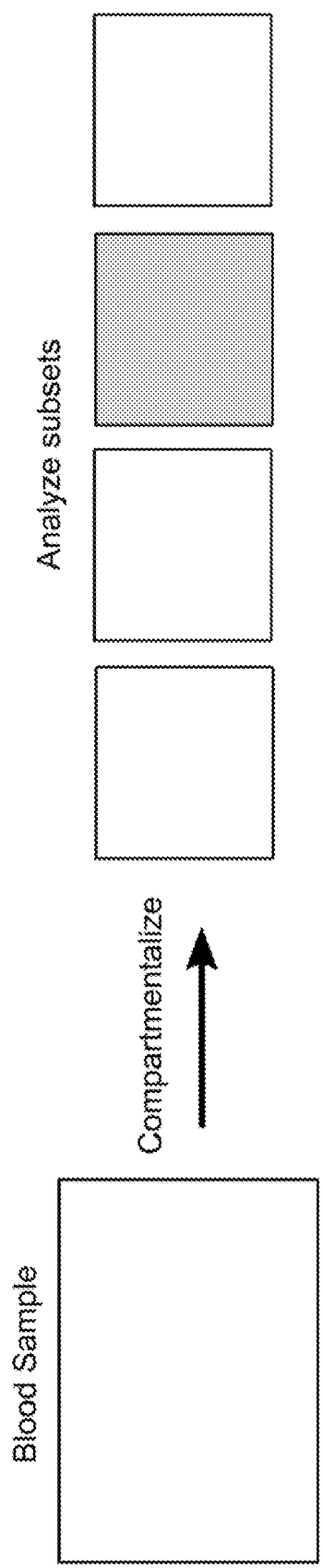
FIG. 8 shows compartmentalization to analyze subsets of blood samples.
Figure 9:
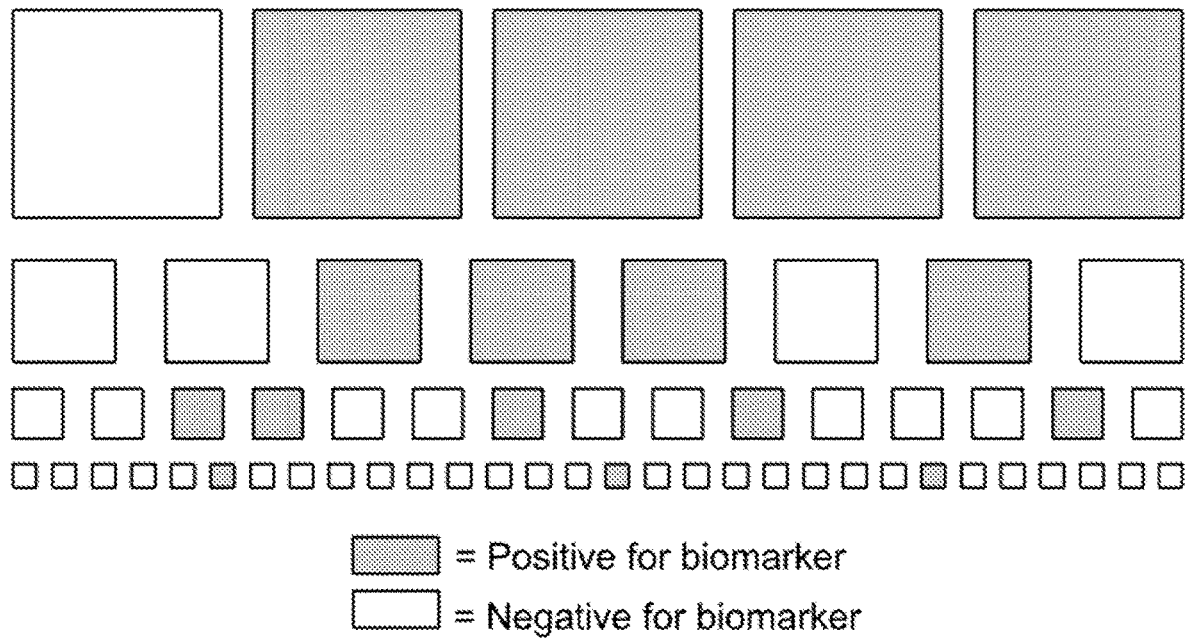
FIG. 9 shows that compartments may be similar or different in size to improve statistical significance and may use a 'most probable number' approach. This is a statistical method for quantifying the number of specimens in a volume based on a reaction that changes the color of the solution.
Figure 10A:
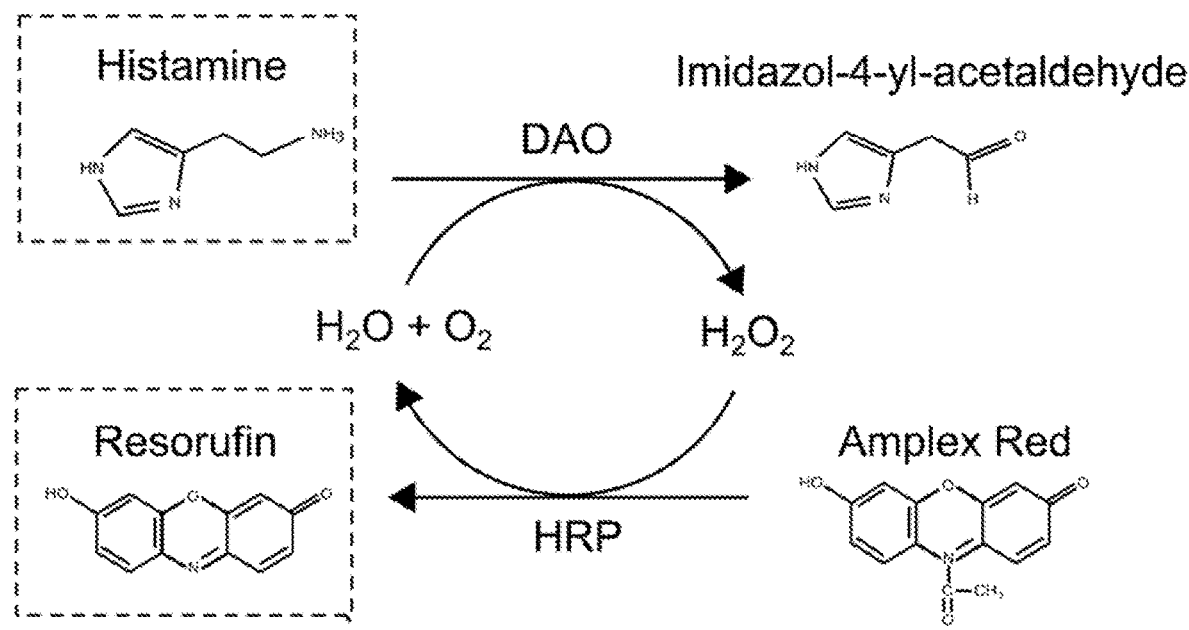
FIG. 10A shows a schematic illustrating a general assay for histamine detection using D-amino acid oxidase (DAO) and Amplex Red.
Figure 10B:
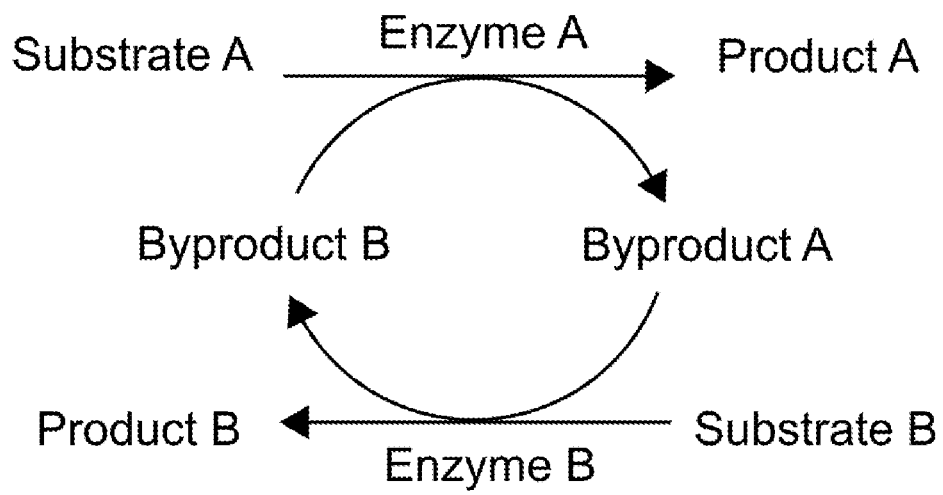
FIG. 10B shows a general coupled or single enzymatic reaction.
Figure 10B:
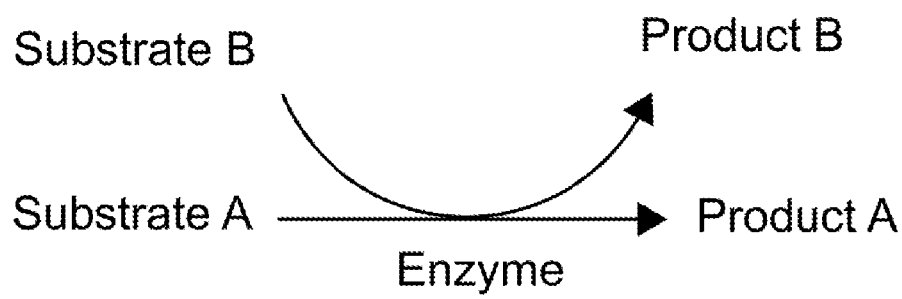
Figure 11A:
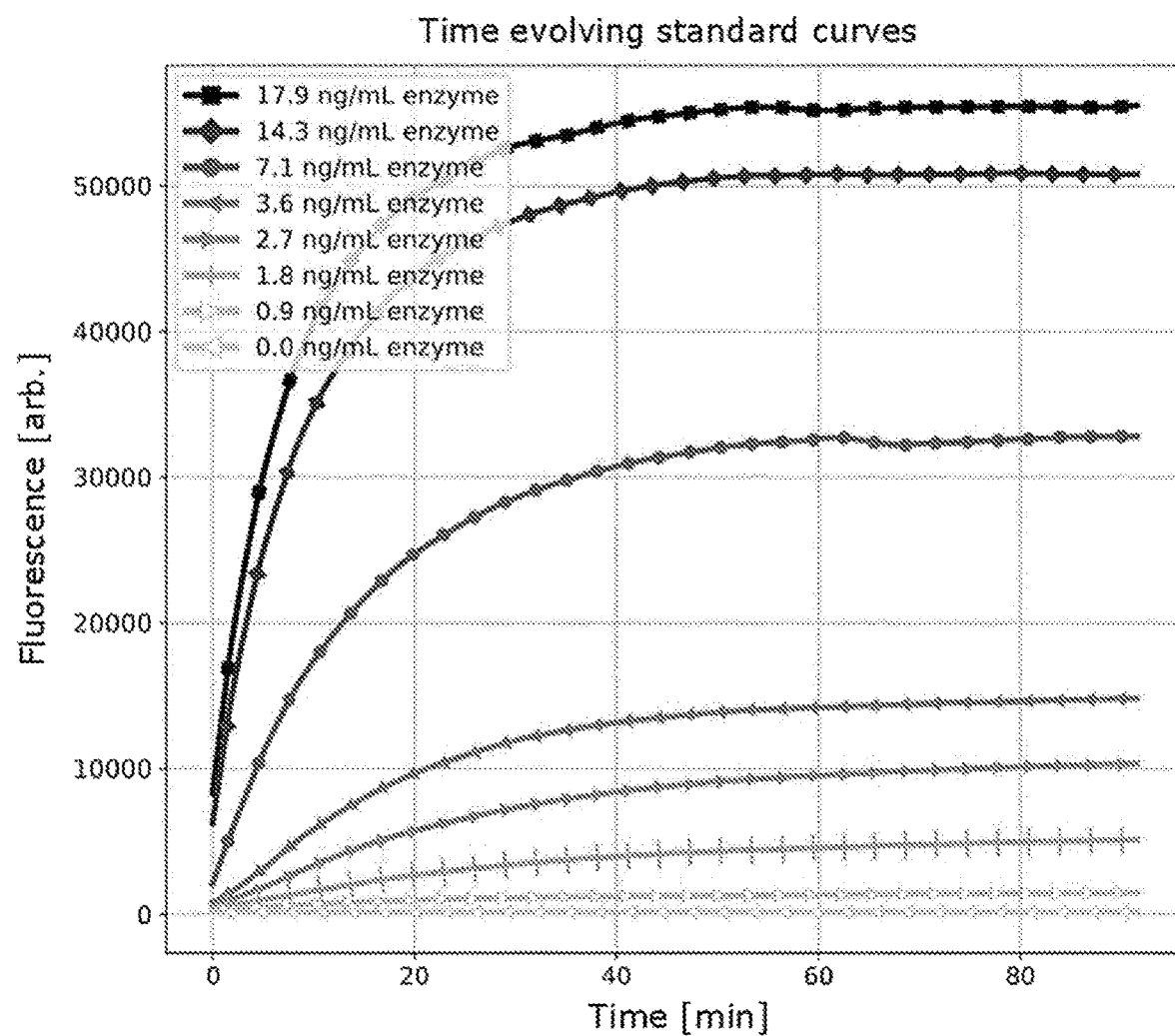
FIGS. 11A-11D show ELISA based BAT readout by measuring the amount of enzyme conjugated activation markers present in activated basophils. Standard curves of known amounts of enzyme conjugated antibody are established to measure this quantity of enzyme conjugated activation markers on basophils.
Figure 11B:
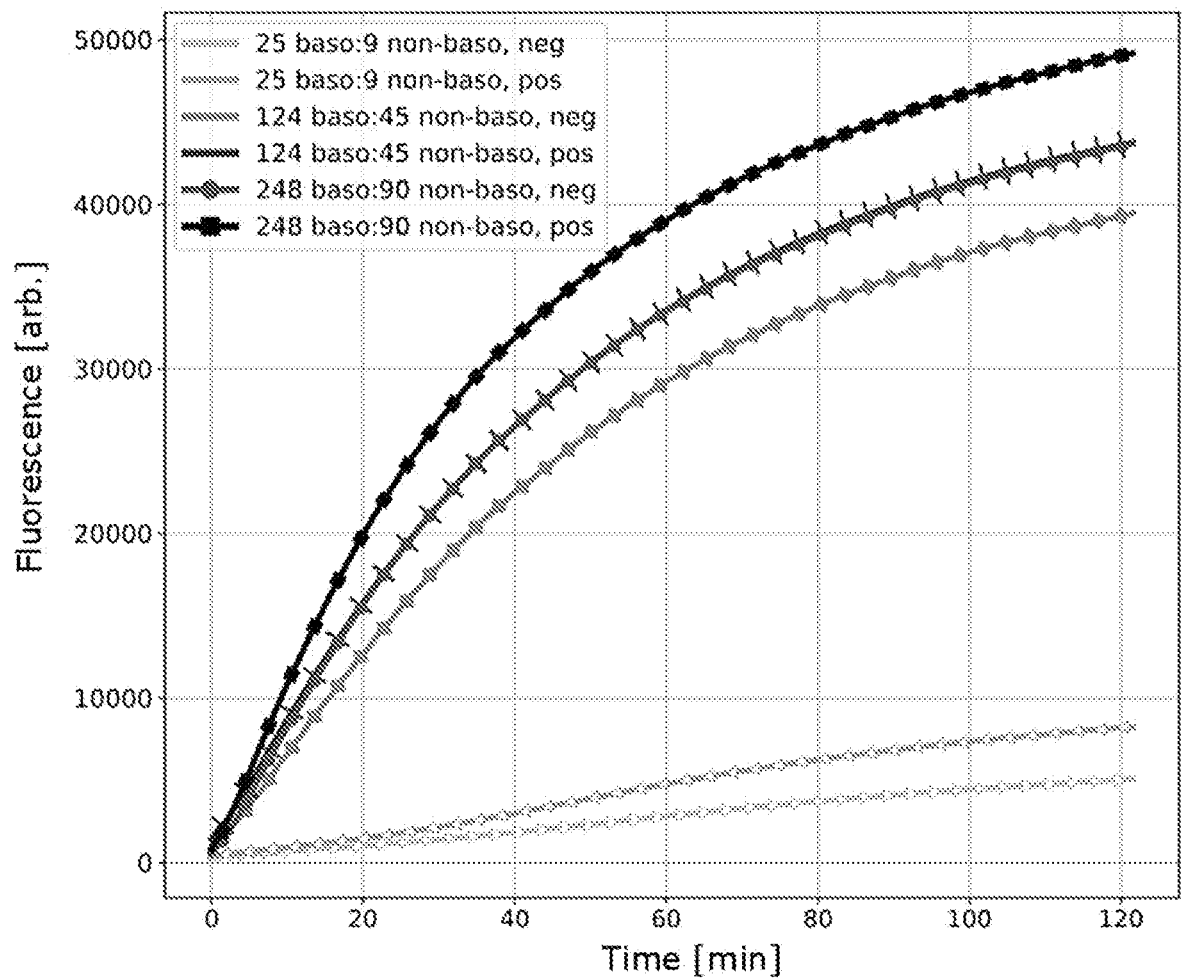
Figure 11C:
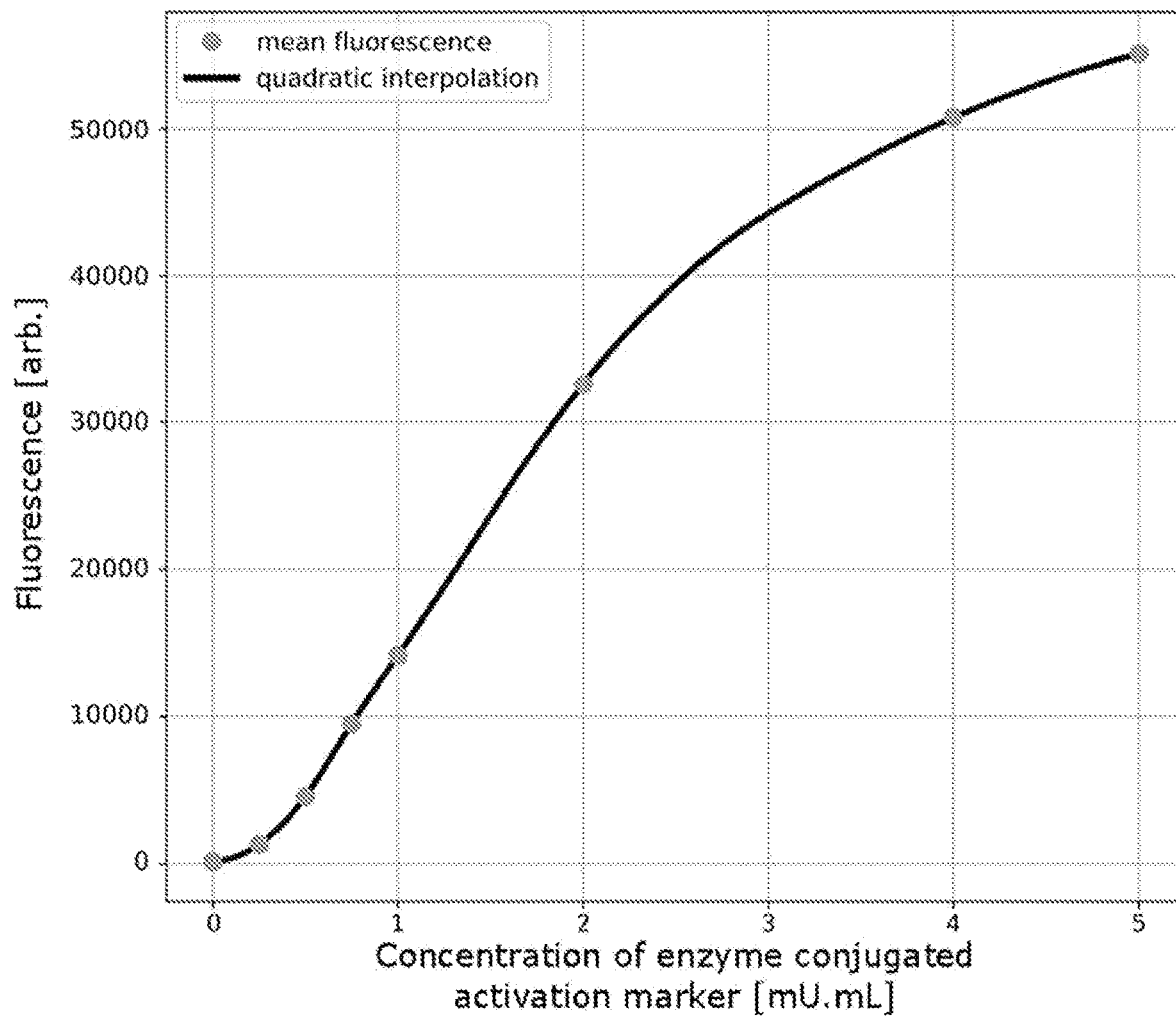
Figure 11D:
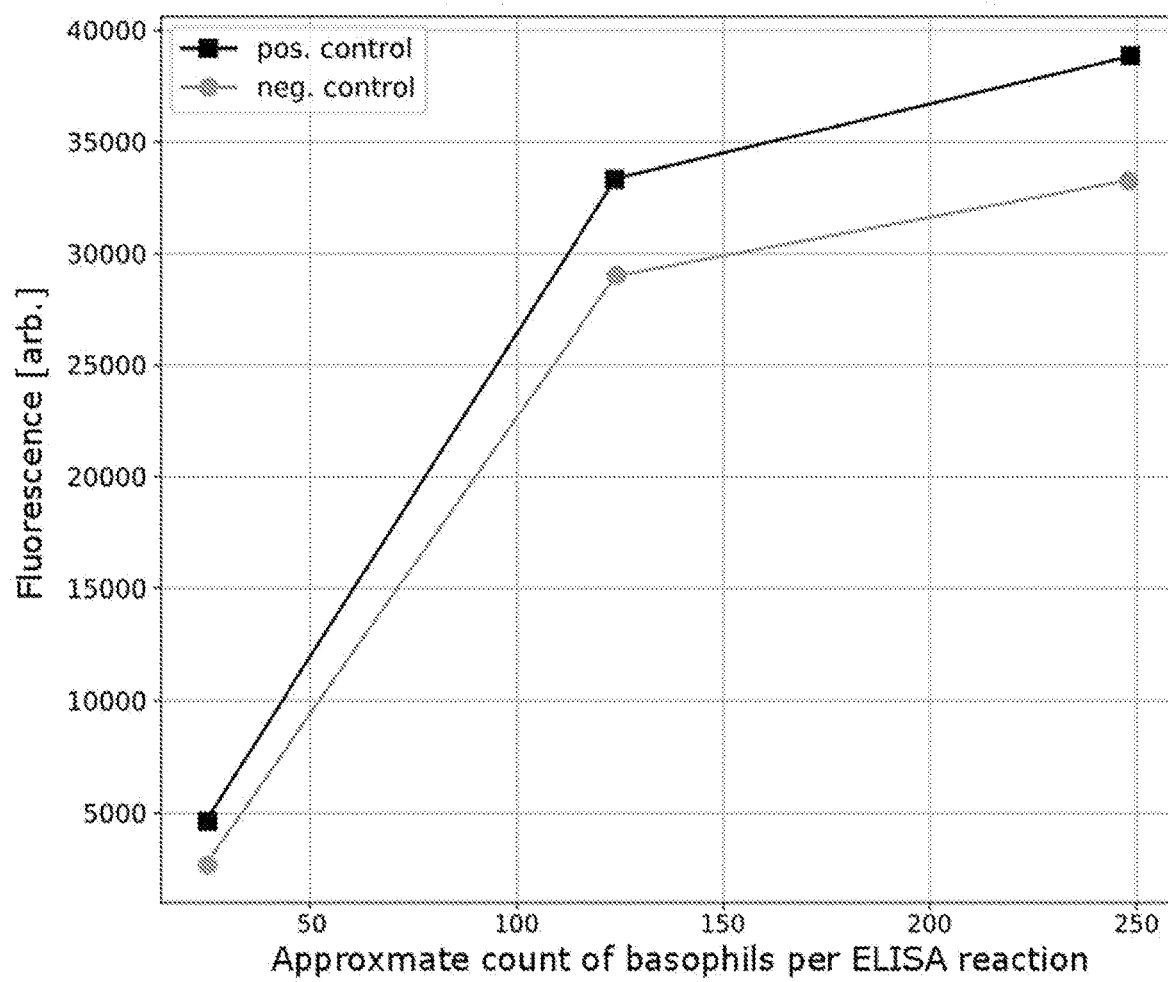
Figure 12:
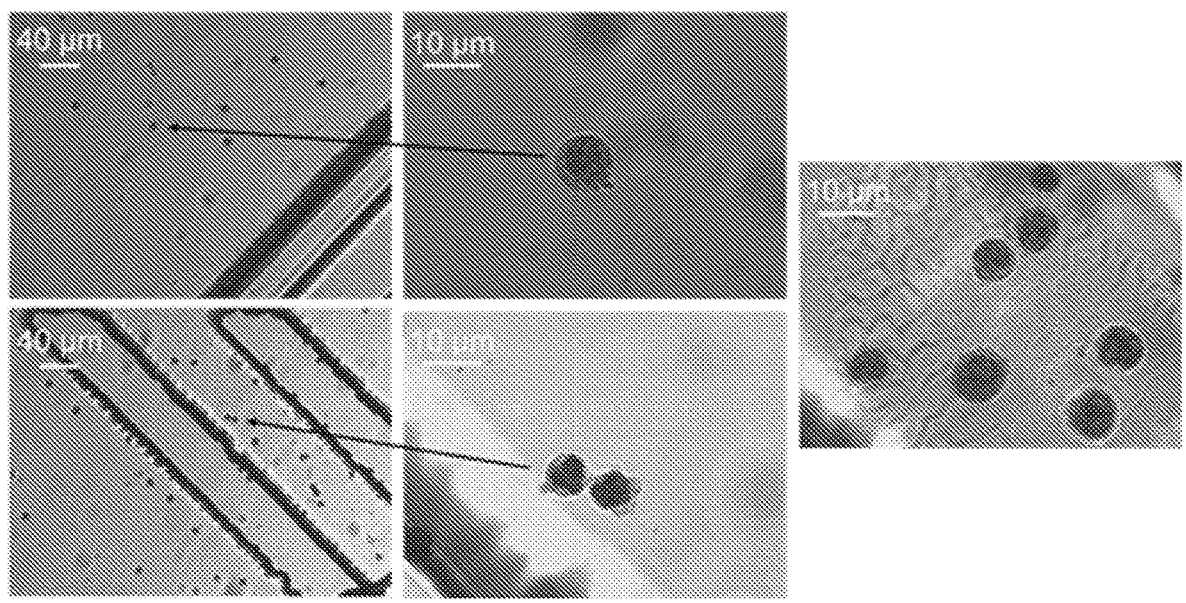
FIG. 12 shows immunocaptured basophils using antibodies specific to basophils.
Figure 13:
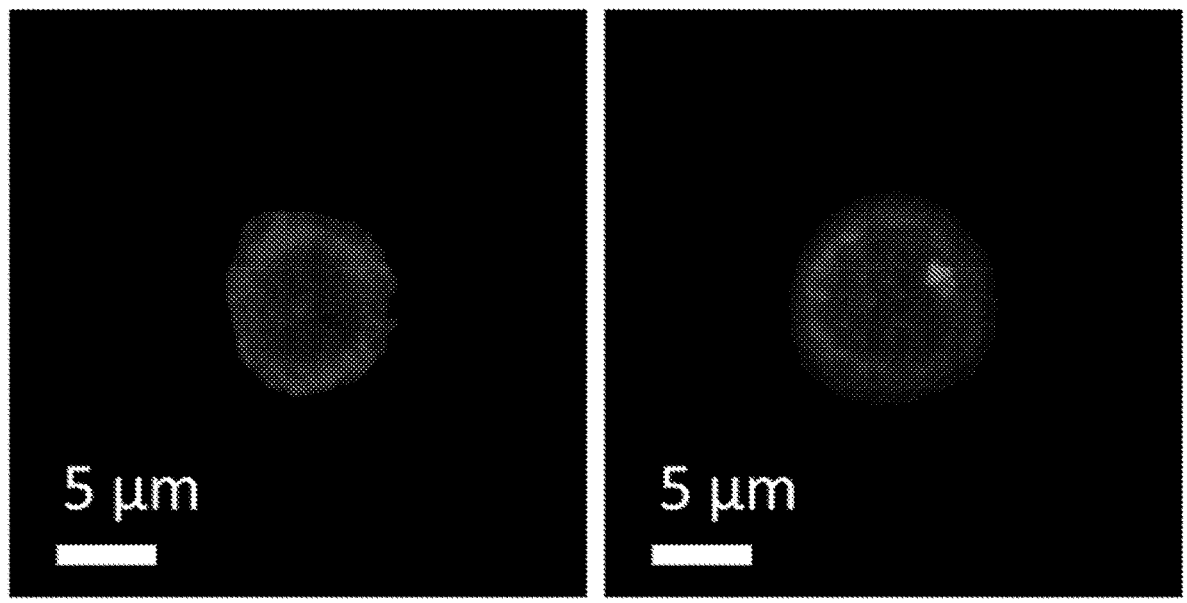
FIG. 13 shows confocal images of unstimulated basophil (left) and stimulated basophil (right). Medium gray indicates CD123 (Alexa Fluor 647). Light gray indicates avidin binding (Alexa Fluor 488).
Figure 14:
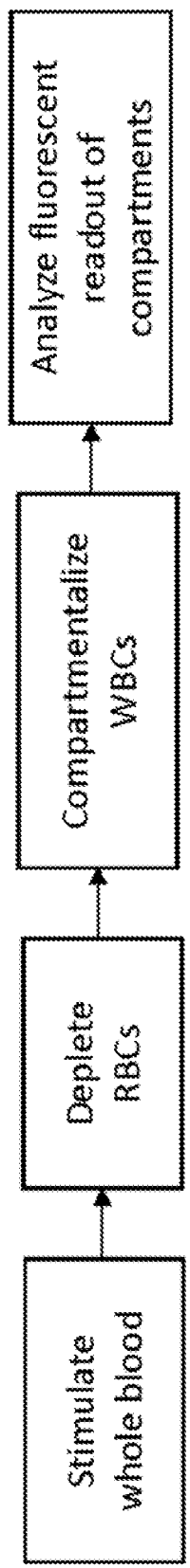
FIG. 14 shows an alternative on-chip process flow without enriching basophils.
Figure 15:
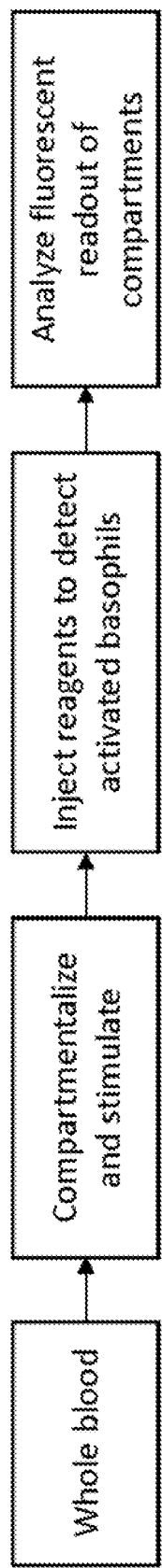
FIG. 15 shows an alternative on-chip process flow using whole blood without removing red blood cells.

In some embodiments, the microfluidic device is designed to compartmentalize discrete volumes of basophils, whole blood, or white blood cells into a plurality of microfluidic compartments (FIG. 8). Partitioning of a sample into compartments may involve distributing any suitable portion including up to the entire sample among the compartments. Each compartment includes a fluid volume that is isolated from the fluid volumes of other compartments. The compartments may be isolated from one another by a fluid phase, such as a continuous phase of an emulsion, by a solid phase, such as at least one wall of the microfluidic device or a container in the microfluidic device, or a combination thereof. The compartments may be in the form of aqueous droplets, where the sample of blood is contained in droplets in oil or some alternative immiscible solution. Droplets may be formed, for example, with a droplet generator or by agitation of the sample. Alternatively, the compartments may be in the form of plugs of fluid, where blood samples are contained in plugs of fluid separated by oil or another immiscible substrate. The compartments may also be in the form of microfluidic wells, microfluidic liquid traps, or microfluidic channels.

The compartments may have any suitable volume or volumes. The compartments may be of substantially uniform volume or may have different volumes. Exemplary compartments having substantially the same volume are monodisperse droplets. Exemplary volumes for the compartments include, without limitation, an average volume of less than about 100, 10 or 1 μL, less than about 100, 10, or 1 nL, or less than about 100, 10, or 1 pL, among others.

The device's compartments may be loaded by capillary action, gravity, centrifugal force, pumps, vacuum, or actuators such as braille pins or pistons. The samples may remain in the compartments for the entirety of the assay or removed for downstream analysis. Interrogation of these compartments may be conducted with optical methods such as fluorescent measurements, absorbance measurements, or some other means of colorimetric detection. The compartments may also be measured with electrical means to interrogate resistivity, impedance, or conductance.

Figure 7A:
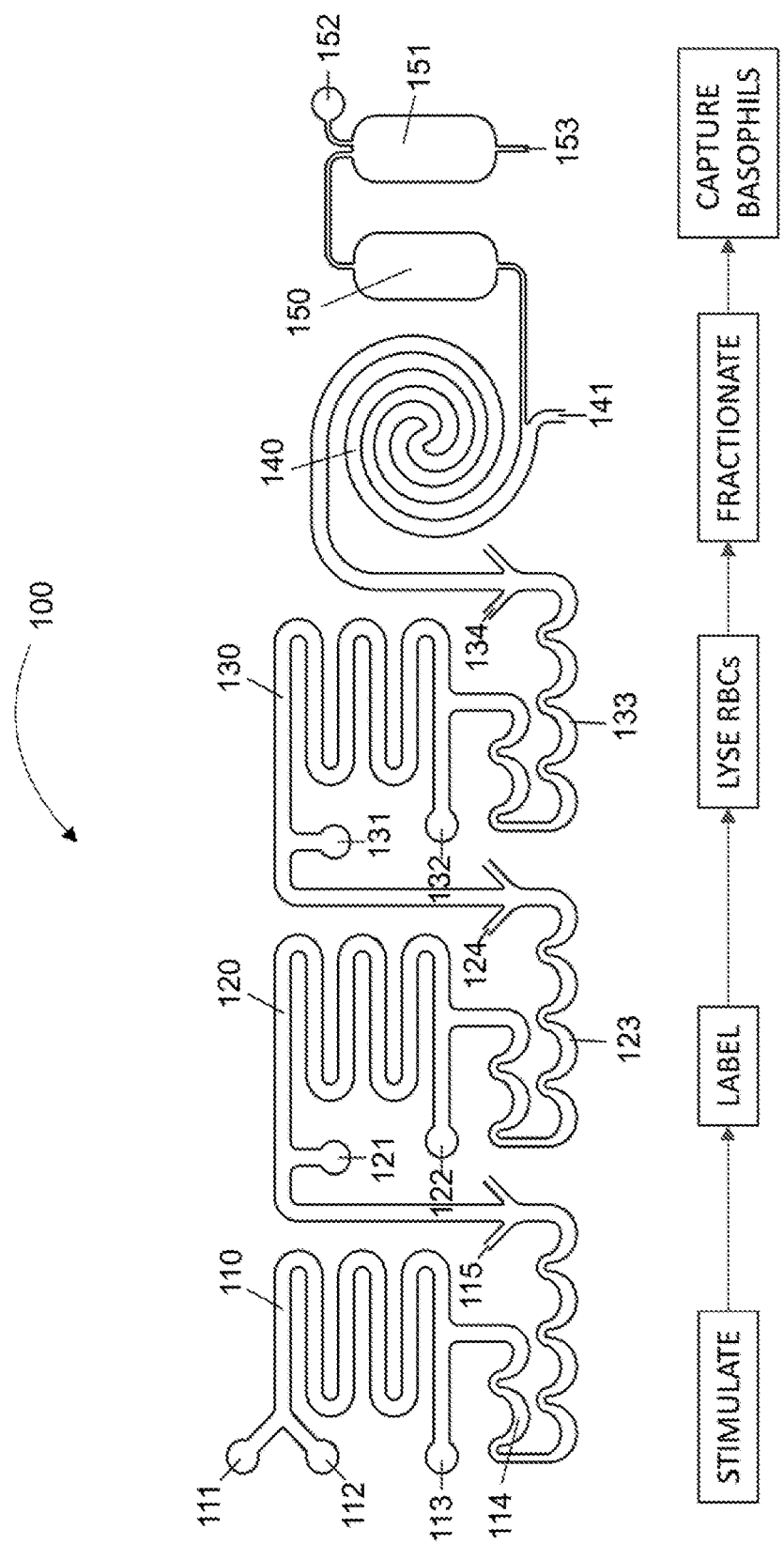
FIGS. 7A-7D show schematics for several microfluidic chip variations with differences in ordering of steps in the on-chip process flow.
Figure 7B:
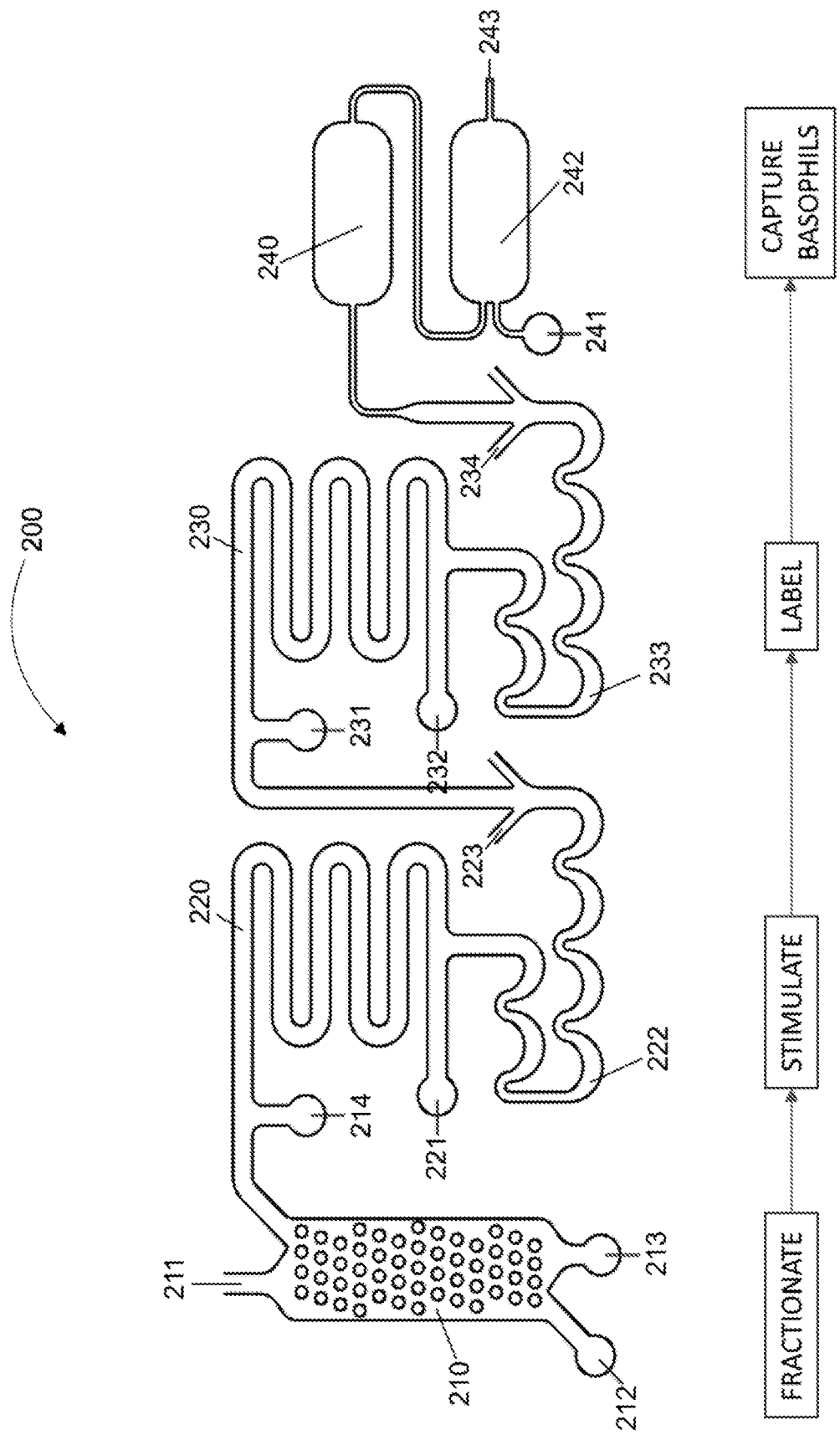
Figure 7C:
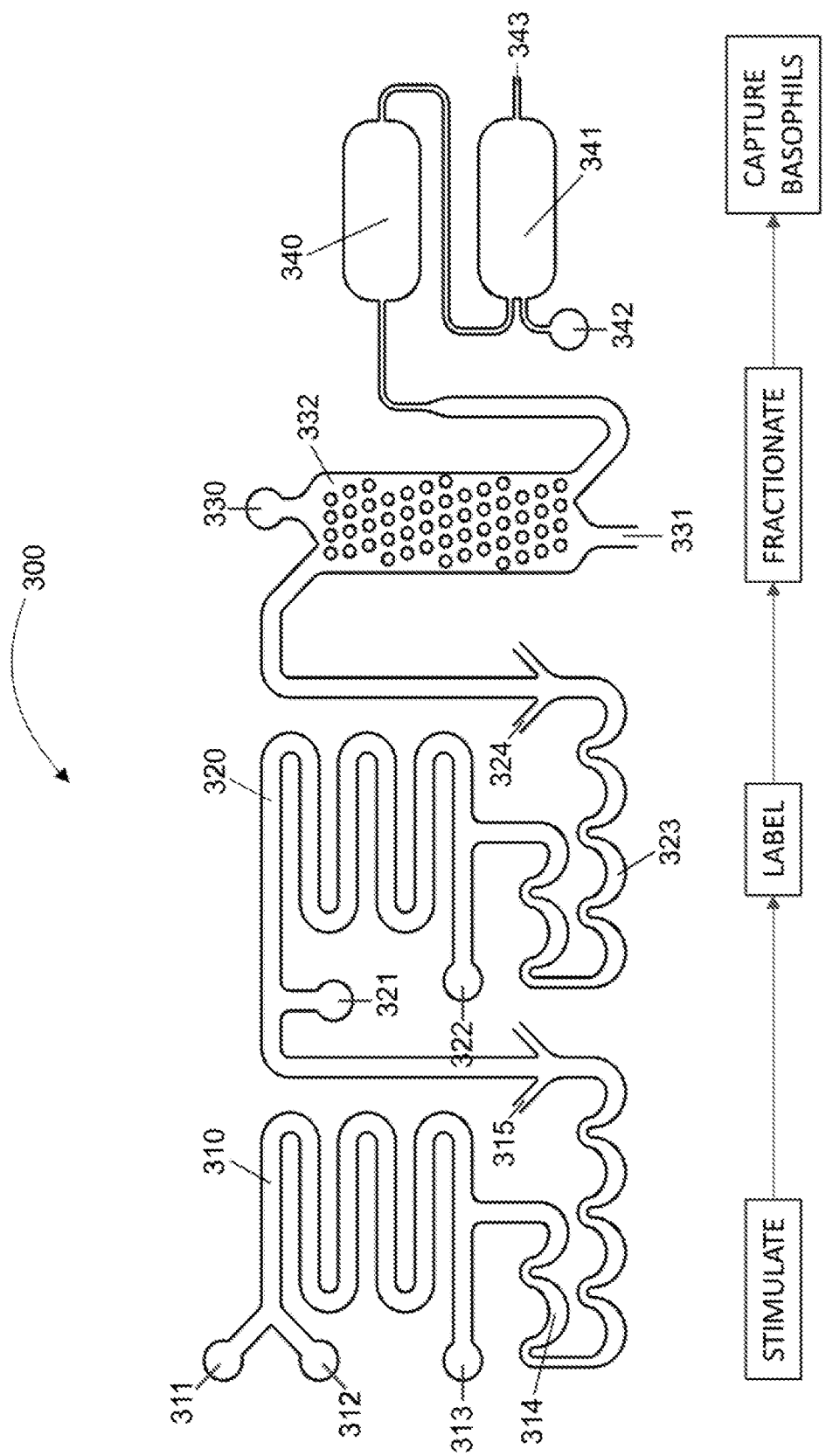
Figure 7D:
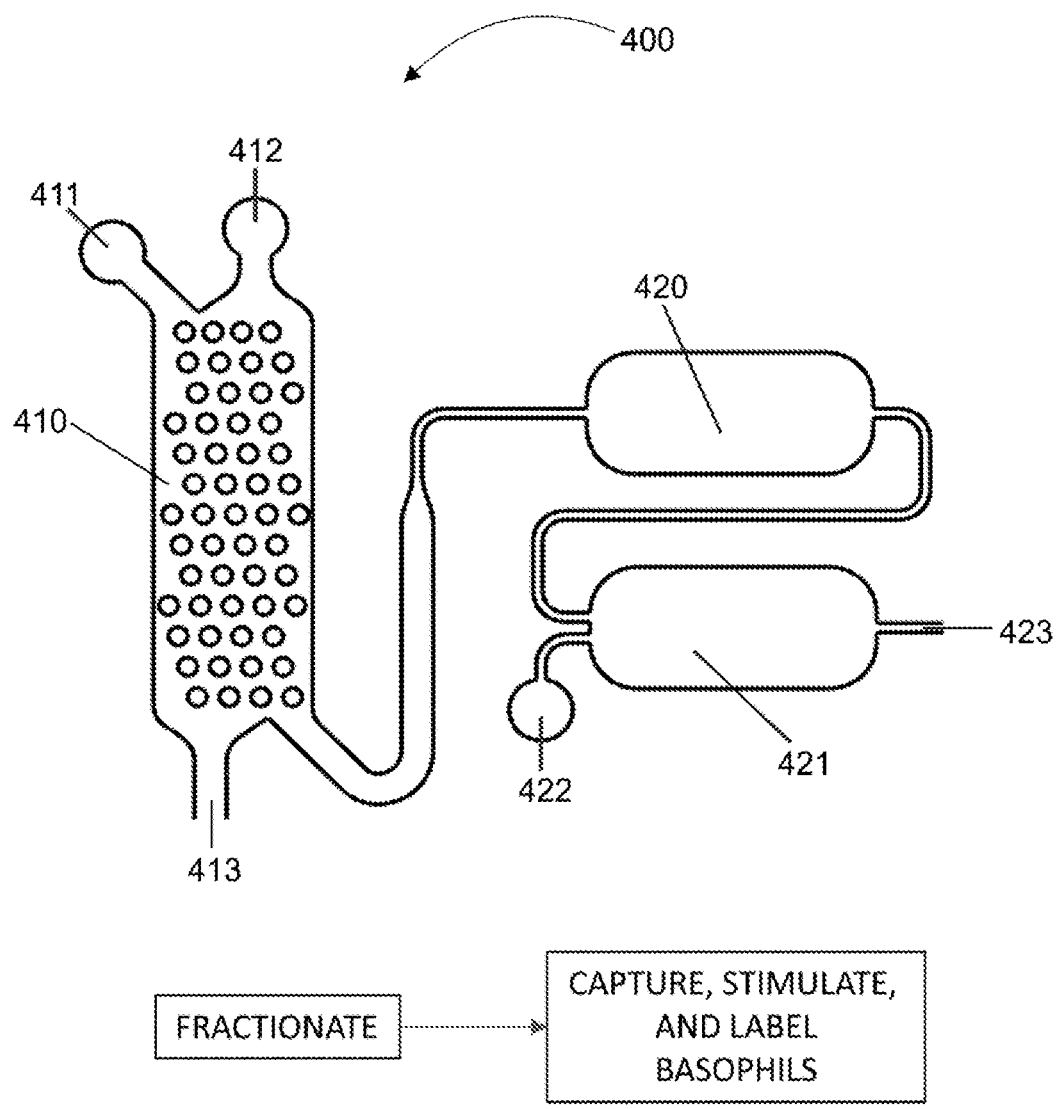

The microfluidic chip can be designed to carry out the steps of the assay in various orders. For example, see FIGS. 7A-7D for schematics of exemplary microfluidic chips designed to carry out assays with differences in the ordering of steps in the on-chip process flow. In one embodiment, the microfluidic chip component 100 comprises: a) a first portion for stimulating basophils comprising: i) a first inlet for loading a blood sample 111, ii) a second inlet for loading an allergen 112, iii) an incubation channel for stimulating the basophils in the blood sample with the allergen 110, wherein the first and second inlets are fluidically connected to the incubation channel 110, iv) a chamber comprising a washing buffer 113, wherein the chamber comprising the washing buffer 113 is fluidically connected to the incubation channel 110, v) a first asymmetric serpentine inertial focusing channel 114, wherein the first asymmetric serpentine inertial focusing channel is fluidically connected to the incubation channel 110, and vi) a first waste outlet 115, wherein the first waste outlet is fluidically connected to the asymmetric serpentine inertial focusing channel 114; b) a second portion for labeling activated basophils comprising: i) a chamber for incubating activated basophils with detectably labeled binding agents that selectively bind to at least one activation marker on the basophils 121, wherein the chamber for incubating activated basophils with detectably labeled binding agents is fluidically connected to the first asymmetric serpentine inertial focusing channel 114, ii) a chamber comprising a wash buffer for removing unbound agents 122, wherein the chamber comprising the wash buffer for removing unbound binding agents is fluidically connected to the chamber for incubating activated basophils with detectably labeled binding agents 121, iii) a channel connecting the chamber for incubating activated basophils with detectably labeled binding agents and the chamber comprising the wash buffer for removing unbound binding agents 120, iv) a second asymmetric serpentine inertial focusing channel 123, wherein the second asymmetric serpentine inertial focusing channel is fluidically connected to the channel connecting the chamber for incubating activated basophils with detectably labeled binding agents 121 and the chamber comprising the wash buffer for removing unbound binding agents 122 and v) a second waste outlet 124, wherein the second waste channel is fluidically connected to the second asymmetric serpentine inertial focusing channel 123; c) a third portion for lysing red blood cells comprising: i) a chamber comprising a lysis buffer 131, wherein the chamber comprising the lysis buffer is fluidically connected to the second asymmetric serpentine inertial focusing channel 123, ii) a chamber comprising a washing buffer 132, iii) a channel 130 connecting the chamber comprising the lysis buffer 131 and the chamber comprising the washing buffer 132, iv) a third asymmetric serpentine inertial focusing channel 133, wherein the third asymmetric serpentine inertial focusing channel is fluidically connected to the channel 130 connecting the chamber comprising the lysis buffer 131 and the chamber comprising the washing buffer 132, v) a third waste outlet 134, wherein the third waste outlet is fluidically connected to the third asymmetric serpentine inertial focusing channel 133; d) a fourth portion for sample fractionation comprising i) an inertial fractionation spiral 140 and ii) a fourth waste outlet 141, wherein the fourth waste outlet is fluidically connected to the inertial fractionation spiral 140; and e) a fifth portion for capturing basophils comprising i) a basophil negative selection chamber 150, ii) a basophil positive selection chamber 151, wherein the basophil positive selection chamber is fluidically connected to the basophil negative selection chamber, iii) a chamber comprising a wash buffer 152, wherein the chamber comprising the wash buffer is fluidically connected to the basophil positive selection chamber, and iv) an exit channel 153, wherein the exit channel is fluidically connected to the basophil positive selection chamber. (See FIG. 7A).

For this embodiment of the microfluidic chip component 100, the assay would be conducted by a method comprising:

a) introducing the blood sample into the first inlet 111; b) introducing the allergen into the second inlet 112; c) flowing the blood sample and the allergen into the incubation channel 110, wherein basophils in the blood sample are exposed to the allergen for a time sufficient to allow activation of any basophil comprising an immunoglobulin E (IgE) specific for the allergen that is bound at an $F_c\varepsilon RI$ receptor; d) flowing the blood sample through the first asymmetric serpentine inertial focusing channel 114 to the chamber for incubating activated basophils with detectably labeled binding agents 121, wherein contacting the activated basophils with said detectably labeled binding agents in said chamber results in said binding agents selectively binding to at least one activation marker on the activated basophils; e) removing the detectably labeled binding agents that have not bound to the activated basophils at said at least one activation marker by washing the basophils with the washing buffer; f) flowing the blood sample through the second asymmetric serpentine inertial focusing channel 123 to the chamber for lysing red blood cells 131, wherein contacting the red blood cells in the blood sample with the lysis buffer lyses the red blood cells; g) flowing the blood sample through the third asymmetric serpentine inertial focusing channel 133 to the inertial fractionation spiral 140, wherein red blood cells are separated from the basophils in the blood sample; h) depleting the blood sample of the red blood cells by expelling the red blood cells out of the fourth waste outlet 141; i) flowing the remaining blood sample to the basophil negative selection chamber 150, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber 151, wherein the basophils are captured by contacting the basophils with the plurality of immobilized binding agents in the basophil positive selection chamber, wherein said binding agents selectively bind to one or more cell surface markers on the basophils.

In another embodiment, the microfluidic chip component 200 comprises: a) a first portion for sample fractionation comprising: i) a first inlet for loading a blood sample 213, ii) a second inlet for loading a running buffer 212, ii) a DLD array 210, wherein the DLD array is fluidically connected to the first inlet 213 and the second inlet 212, and ii) a first waste outlet 211, wherein the first waste outlet is fluidically connected to the DLD array 210; b) a second portion for stimulating basophils comprising: i) a chamber comprising the allergen 214, wherein the chamber comprising the allergen is fluidically connected to the DLD array 210, ii) an incubation channel for stimulating the basophils in the blood sample with the allergen 220, wherein the incubation channel is fluidically connected to the chamber comprising the allergen 214, iv) a chamber comprising a washing buffer 221, wherein the chamber comprising the washing buffer is fluidically connected to the incubation channel 220, v) a first asymmetric serpentine inertial focusing channel 222, wherein the first asymmetric serpentine inertial focusing channel is fluidically connected to the incubation channel 220 and vi) a second waste outlet 223, wherein the second waste outlet is fluidically connected to the first asymmetric serpentine inertial focusing channel 222; c) a third portion for labeling activated basophils comprising: i) a chamber for incubating activated basophils with detectably labeled binding agents that selectively bind to at least one activation marker on the basophils 231, wherein the chamber for incubating activated basophils with detectably labeled binding agents is fluidically connected to the first asymmetric serpentine inertial focusing channel 222, ii) a chamber comprising a washing buffer for removing unbound agents 232, iii) a channel 230 connecting the chamber for incubating activated basophils with detectably labeled binding agents 231 and the chamber comprising a washing buffer for removing unbound binding agents 232, iv) a second asymmetric serpentine inertial focusing channel 233, wherein the second asymmetric serpentine inertial focusing channel is fluidically connected to the channel 230 connecting the chamber for incubating activated basophils with detectably labeled binding agents 231 and the chamber comprising the washing buffer for removing unbound binding agents 232 and v) a third waste outlet 234, wherein the third waste outlet is fluidically connected to the second asymmetric serpentine inertial focusing channel 233; and d) a fourth portion for capturing basophils comprising i) a basophil negative selection chamber 240, ii) a basophil positive selection chamber 242, wherein the basophil positive selection chamber is fluidically connected to the basophil negative selection chamber, iii) a chamber comprising a wash buffer 241, wherein the chamber comprising the wash buffer is fluidically connected to the basophil positive selection chamber 242, and iv) an exit channel 243, wherein the exit channel is fluidically connected to the basophil positive selection chamber 242. (See FIG. 7B.)

For this embodiment of the microfluidic chip component 200, the assay would be conducted by a method comprising: a) introducing the blood sample into the first inlet 213; b) introducing the running buffer into the second inlet 212; c) flowing the blood sample through the DLD array 210, wherein the red blood cells are separated from the basophils in the blood sample; d) depleting the blood sample of the red blood cells by expelling the red blood cells out of the first waste outlet 211; e) flowing the blood sample into the chamber comprising the allergen 214; f) flowing the blood sample and the allergen into the incubation channel 220, wherein basophils in the blood sample are exposed to the allergen for a time sufficient to allow activation of any basophil comprising an immunoglobulin E (IgE) specific for the allergen that is bound at an $F_c\varepsilon RI$ receptor; g) flowing the blood sample through the first asymmetric serpentine inertial focusing channel 222 to the chamber for incubating activated basophils with detectably labeled binding agents 231, wherein contacting the activated basophils with said detectably labeled binding agents in said chamber results in said binding agents selectively binding to at least one activation marker on the activated basophils; h) removing the detectably labeled binding agents that have not bound to the activated basophils at said at least one activation marker by washing the basophils with the washing buffer; i) flowing the remaining blood sample to the basophil negative selection chamber 240, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber 242, wherein the basophils are captured by contacting the basophils with the plurality of immobilized binding agents in the basophil positive selection chamber, wherein said binding agents selectively bind to one or more cell surface markers on the basophils.

In another embodiment, the microfluidic chip component 300 comprises: a) a first portion for stimulating basophils comprising: i) a first inlet for loading a blood sample 311, ii) a second inlet for loading an allergen 312, iii) an incubation channel for stimulating the basophils in the blood sample with the allergen 310, wherein the first and second inlets are fluidically connected to the incubation channel, iv) a chamber comprising a washing buffer 313, wherein the chamber comprising the washing buffer is fluidically connected to the incubation channel 310, v) a first asymmetric serpentine inertial focusing channel 314, wherein the first asymmetric serpentine inertial focusing channel is fluidically connected to the incubation channel 310, and vi) a first waste outlet 315, wherein the first waste outlet is fluidically connected to the asymmetric serpentine inertial focusing channel 314; b) a second portion for labeling activated basophils comprising: i) a chamber for incubating activated basophils with detectably labeled binding agents that selectively bind to at least one activation marker on the basophils 321, wherein the chamber for incubating activated basophils with detectably labeled binding agents is fluidically connected to the first asymmetric serpentine inertial focusing channel 314, ii) a chamber comprising a washing buffer for removing unbound binding agents 322, iii) a channel 320 connecting the chamber for incubating activated basophils with detectably labeled binding agents 321 and the chamber comprising a washing buffer for removing unbound binding agents 322, iv) a second asymmetric serpentine inertial focusing channel 323, wherein the second asymmetric serpentine inertial focusing channel is fluidically connected to the channel 320 connecting the chamber for incubating activated basophils with detectably labeled binding agents 321 and the chamber comprising the washing buffer for removing unbound binding agents 322, and v) a second waste outlet 324, wherein the second waste outlet is fluidically connected to the second asymmetric serpentine inertial focusing channel 323; c) a third portion for sample fractionation comprising: i) a DLD array 332, wherein the DLD array is fluidically connected to the second asymmetric serpentine inertial focusing channel 323, ii) a chamber comprising a running buffer 330, wherein the chamber comprising the running buffer is fluidically connected to the DLD array 332, and ii) a third waste outlet for expelling red blood cells and platelets 331, wherein the third waste outlet is fluidically connected to the DLD array 332; and d) a fourth portion for capturing basophils comprising i) a basophil negative selection chamber 340, ii) a basophil positive selection chamber 341, wherein the basophil positive selection chamber is fluidically connected to the basophil negative selection chamber, iii) a chamber comprising a washing buffer 342, wherein the chamber comprising the washing buffer is fluidically connected to the basophil positive selection chamber 341, and iv) an exit channel 343, wherein the exit channel is fluidically connected to the basophil positive selection chamber 341. (See FIG. 7C.)

For this embodiment of the microfluidic chip component 300, the assay would be conducted by a method comprising: a) introducing the blood sample into the first inlet 311; b) introducing the allergen into the second inlet 312; c) flowing the blood sample and the allergen into the incubation channel 310, wherein basophils in the blood sample are exposed to the allergen for a time sufficient to allow activation of any basophil comprising an immunoglobulin E (IgE) specific for the allergen that is bound at an $F_c\varepsilon RI$ receptor; d) flowing the blood sample through the first asymmetric serpentine inertial focusing channel 314 to the chamber for incubating activated basophils with detectably labeled binding agents 321, wherein contacting the activated basophils with said detectably labeled binding agents in said chamber results in said binding agents selectively binding to at least one activation marker on the activated basophils; e) removing the detectably labeled binding agents that have not bound to the activated basophils at said at least one activation marker by washing the basophils with the washing buffer; f) flowing the blood sample through the second asymmetric serpentine inertial focusing channel 323; g) flowing the blood sample through the DLD array 332, wherein the red blood cells are separated from the basophils in the blood sample; h) depleting the blood sample of the red blood cells by expelling the red blood cells out of the third waste outlet 331; i) flowing the remaining blood sample to the basophil negative selection chamber 340, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and j) flowing the blood sample to the basophil positive selection chamber 341, wherein the basophils are captured by contacting the basophils with the plurality of immobilized binding agents in the basophil positive selection chamber 341, wherein said binding agents selectively bind to one or more cell surface markers on the basophils.

In another embodiment, the microfluidic chip component 400 comprises: a) a first portion for sample fractionation comprising: i) a first inlet for loading a blood sample 411, ii) a second inlet for loading a running buffer 412, ii) a DLD array 410, wherein the DLD array is fluidically connected to the first inlet 411 and the second inlet 412, and ii) a first waste outlet for expelling red blood cells and platelets 413, wherein the first waste outlet is fluidically connected to the DLD array 410; and b) a second portion for capturing, stimulating, and labeling basophils comprising: i) a basophil negative selection chamber 420, ii) a basophil positive selection chamber 421, wherein the basophil positive selection chamber is fluidically connected to the basophil negative selection chamber 420, iii) a chamber comprising an allergen 422, wherein the chamber comprising the allergen is fluidically connected to the basophil positive selection chamber 421, and iv) a second waste outlet 423. (See FIG. 7D.)

For this embodiment of the microfluidic chip component 400, the assay would be conducted by a method comprising: a) introducing the blood sample into the first inlet 411; b) introducing the running buffer into the second inlet 412; c) flowing the blood sample through the DLD array 410, wherein the red blood cells are separated from the basophils in the blood sample; d) depleting the blood sample of the red blood cells by expelling the red blood cells out of the first waste outlet 413; e) flowing the remaining blood sample to the basophil negative selection chamber 420, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; f) flowing the blood sample to the basophil positive selection chamber 421, wherein the basophils are captured by contacting the basophils with the plurality of immobilized binding agents in the basophil positive selection chamber, wherein said binding agents selectively bind to one or more cell surface markers on the basophils; g) flowing the blood sample into the chamber comprising the allergen 422, wherein basophils in the blood sample are exposed to the allergen for a time sufficient to allow activation of any basophil comprising an immunoglobulin E (IgE) specific for the allergen that is bound at an $F_c\varepsilon RI$ receptor; h) adding detectably labeled binding agents that selectively binding to at least one activation marker on the activated basophils to the chamber comprising the allergen and the activated basophils; and i) removing the detectably labeled binding agents that have not bound to the activated basophils at said at least one activation marker by washing the basophils with the washing buffer.

Additionally, microfluidic devices described herein can be adapted for multiplexed detection of allergic responses to multiple allergens by performing assays in parallel to detect basophil responses to each allergen. For example, the microfluidic device may comprise multiple chambers, each comprising a different allergen that can be tested for its ability to activate basophils utilizing the devices and diagnostic methods described herein. In certain embodiments, the microfluidic device includes several parallel channels and chambers for separately analyzing activation of basophils from the same sample upon stimulation by the different allergens, and a series of detector or sensor units for detecting basophil activation in response to stimulation by the different allergens. Basophils from a single blood sample may be divided among the parallel channels and chambers to allow simultaneous analysis of the response to different allergens.

Kits

Also provided are kits comprising a microfluidic device for use in allergy testing as described herein. The subject kits may further comprise allergens for testing, detectably labeled binding agents for detecting activation of basophils (e.g., fluorescently labeled anti-CD63 antibodies, anti-CD203 antibodies, or anti-avidin antibodies, or fluorescently labeled avidin), basophil capture agents (e.g., an anti-CD123 antibody, an anti-CD193 antibody, an anti-CD294 antibody, an anti-CCR3 antibody, an anti-CD192 antibody, and an anti-IgE antibody), non-basophil capture agents (e.g., an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody), buffers, and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

The devices and diagnostic methods for allergy testing disclosed herein are useful for screening candidate allergens for potential allergic responses and accurately predict the severity of allergic reactions in individuals. Furthermore, the devices and methods can be conveniently used for allergy screening at a hospital, for example, in a doctor's office or an emergency room, or at home. Patients who experience adverse allergic reactions to allergens can be quickly screened to determine the source of the problem such that repeated exposure to allergens can be avoided.

The devices and diagnostic methods described herein are also useful in monitoring the progress of treatment of patients undergoing food immunotherapy. Although a subject may need to completely avoid foods that cause adverse allergic reactions, increased tolerance of a problem food may be achieved by administering slowly small but steadily increasing doses of the problem food until the patient is desensitized to it. Allergy testing can be performed using the devices and methods described herein to determine whether food immunotherapy has been effective in achieving food allergy desensitization.

Candidate allergens that can be tested by the methods described herein include any type of allergen, including ingested allergens, inhaled allergens, occupational allergens, environmental allergens, or any other substance that triggers a harmful immune reaction resulting in activation of basophils. Blood samples may be tested with various candidate allergens to test for various types of allergies such as, but not limited to, a food allergy (e.g., strawberries and other fruits and vegetables, peanuts, soy, and other legumes, walnuts and other treenuts, shellfish and other seafood, milk and other dairy products, wheat and other grains, and eggs), an animal allergy (e.g., cat), a cockroach allergy, a tick allergy, a dust mite allergy, an insect sting allergy (e.g. (bee, wasp, and others), a latex allergy, a medication allergy (e.g., penicillin, carboplatin), mold and fungi allergies (e.g., *Alternaria alternata, Aspergillus* and others), a pollen allergy (e.g., ragweed, Bermuda grass, Russian thistle, oak, rye, and others), and a metal allergy.

Sets of allergens may be tested including, without limitation, environmental allergens, e.g. pollens; insect allergens, e.g. bee venom, spider venom, etc.; food allergens, e.g. fish, shellfish (shrimp, crab, lobster, oyster, scallops), soy, strawberries, tree nuts (walnut, hazel/filbert, cashew, pistachio, Brazil, pine nut, almond), peanuts, milk, egg protein, etc.; drug allergens, e.g. penicillin, etc. For example, a panel of insect allergens may comprise epitopes from a plurality of insect venoms, e.g. *Myrmecia pilosula; Apis mellifera* bee venom phospholipase A2 (PLA2) and antigen 5S; phospholipases from the yellow jacket *Vespula maculifrons* and white-faced hornet *Dolichovespula maculate*, etc. A panel of pollen allergens may comprise epitopes from a plurality of plants, e.g. birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., *gramineae*, etc.

The compositions and methods of the invention are applicable to a variety of allergens, including food allergens; environmental allergens; animal allergens; etc. Allergens include, e.g. pollens; insect allergens, e.g. bee venom, spider venom, etc.; food allergens, e.g. fish, shellfish (shrimp, crab, lobster, oyster, scallops), soy, strawberries, tree nuts (walnut, hazel/filbert, cashew, pistachio, Brazil, pine nut, almond), peanuts, milk, egg protein, etc.; drug allergens, e.g. penicillin, etc. Insect venoms include, e.g. *Myrmecia pilosula; Apis mellifera* bee venom phospholipase A2 (PLA2) and antigen 5S; phospholipases from the yellow jacket *Vespula maculifrons* and white-faced hornet *Dolichovespula maculate*, etc.

Pollen allergens may comprise epitopes from a plurality of plants, e.g. birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., *gramineae*, etc.

Allergens of interest for analysis by the methods of the invention include, without limitation, allergens associated with anaphylaxis, which include food allergens, insect allergens and drug allergens. Allergens known to be associated with anaphylaxis include food allergens: peanuts, tree nuts, fish, shellfish, cow's milk, soy, and eggs; insect allergens, particularly from stinging insects, e.g. honeybees, fire ants, yellow jackets, yellow hornets and paper wasps; drugs: β-lactams; nonsteroidal anti-inflammatory drugs (NSAIDs); biologic modifiers, e.g. cetuximab, infliximab and omalizumab. Suitable panels comprising an epitope array from one or more of these allergens are provided.

Other allergens of interest are those responsible for allergic dermatitis caused by blood sucking arthropods, e.g. *Diptera*, including mosquitos (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order *Siphonaptera*, including the genera *Xenopsylla, Pulex* and *Ctenocephalides felis*.

Some specific allergens of interest include egg proteins, which can be provided in a panel of egg protein epitopes from one, two, three, four or more different egg proteins; in combination with a panel of food allergens; etc. Egg allergens include, e.g. Ovomucoid (Gal d1), 210 aa protein; Genbank Accession: P01005.1; Ovalbumin (Gal d2), AltName: Egg Albumin, Plakalbumin, 386 aa protein; Genbank Accession: P01012.2; Ovotransferin (Gal d3), AltName: Conalbumin, Serumtransferrin, 705 aa protein; Genbank Accession: P02789.2; Lysozyme C (Gal d4), AltName: 1,4-beta-N-acetylmuramidase C, 147 aa protein; Genbank Accession: P00698.1; Alpha-livetin (Gal d5), 615 aa protein, Genbank Accession: P19121.2; etc.

Some specific allergens of interest include peanut proteins, which can be provided in a panel of peanut protein epitopes from one, two, three, four or more different peanut proteins; in combination with a panel of food allergens; etc. Peanut allergens include, e.g. Ara h1 (614 a.a); Ara h2.0101 or Ara h2.0201/Conglutin-7/2S albumin(172 a.a)k Ara h3 Glycinin Uniprot 082580; Ara h4 Glycinin seed storage protein Uniprot 5712199; Ara h5 profilin Uniprot Q9SQ19); Ara h6 Conglutin homolog uniprot 5923742; Ara h7 Conglutin homolog uniprot 5923742; Ara h8 Ara h8.0101/PR-10 protein uniprot Q6VT83; Ara h8.0201/PR-10 protein uniprot B0YIU5; Ara h9 Ara h LTP isoallergen precursor; etc.

Some specific allergens of interest include cow's milk proteins, which can be provided in a panel of milk protein epitopes from one, two, three, four or more different milk proteins; in combination with a panel of food allergens; etc. Milk allergens include, Bos Casein βeta-A1 (Uniprot 162797/162805/162931/459292); βeta-A3 Uniprot 459292); αS1 Uniprot 162929; αS2; Kappa uniprot 162811, Beta-lactoglobulin; Alpha-lactalbumin, etc.

Some specific allergens of interest include shellfish proteins, which can be provided in a panel of shellfish protein epitopes from one, two, three, four or more different shellfish proteins; in combination with a panel of food allergens; etc. Shellfish allergens include shrimp tropomyosin: Cra c1 accession D7F1J4; Lit v1 accession B4YAH6; Met e1 accession Q25456; Pan b1 accession P86704, Pen a1 accession AAZ76743.1, Pen i1 tropomyosin; shrimp arginine kinase: Cra c2 accession D7F1J5; Lit v2, accession Q004B5; Pen m2, accession E7CGC2; shrimp sarcoplasmic calcium-binding protein: Cra c4, accession D7F1P9; Pen e4; Pen m4 accession E7CGC4; Lit v4 accession C7A639; shrimp myosin light chain: Art fr 5, accession A7L499; Cra c5, accession D7F1Q1; Lit v3, accession B7SNI3, Pen m3, accession E1A683; shrimp troponin C: Pen m6, accession E7CGC5; Cra c6, accession D7F1Q2; triosephosphate isomerase Cra c8, accession D7F1Q0. Crab allergens include tropomyosin: Cha f 1, accession Q9N2R3; Chi o1, accession A2V735; TPM_CHIOP; Can p 1; Eri i 1; Par c 1; Por s 1; Por tr 1; Ran ra 1; Scy o 1, accession A1KYZ3; Scy pa 1; Scy s 1, accession A7L5V2; arginine kinase Chi o2, accession C9EIP1; Scy s 2; Lim p 2 accession P51541; troponin: Chi o 6, accession P86910; Sarcoplasmic calcium-binding protein: Chi o 4, accession P86909. Lobster allergens include tropomyosin: Hom a1 accession O44119.1; Pan s 1 accession O61379.1; arginine kinase: Hom g 2 accession P14208.4; myosin light chain 2: Hom a3 accession EH115965; troponin C: om a6 accession P29291; sarcoplasmic calcium-bindingL Hom a4. Crayfish allergens include tropomyosin: Pro cl i accession ACN87223.1; sarcoplasmic calcium-binding protein: Pon I4 accession P05946; troponin I: Pon I7 accession P05547. Krill allergens include tropomypsin: Eup p1 accession BAF76431.1; Eup s 1 accession dbj|BAF95205.1. Mollusk allergens include tropomyosin: Hel as 1 accession CAB38044; Hal a 1 accession AAP85231.1; Tod p 1 accession Q9BLG0.3; hemocyanin: Meg C accession CAG28309.2; paramyosin: Hal di accession BAJ61596.1; Myt g accession BAA36517.1; Oct v; Tur c; Hal r.

Some specific allergens of interest include soy proteins, which can be provided in a panel of soy protein epitopes from one, two, three, four or more different soy proteins; in combination with a panel of food allergens; etc. Soy allergens include Gly m 5 Glycine Beta-conglycinin accession CAA35691.1; Gly m 5 Glycine Beta-conglycinin accession AAA33947.1; Gly m 5 Glycine Beta-conglycinin accession AAB01374.1; Gly m 5 Glycine Beta-conglycinin accession AAB23463.1; Glycine Gly m 1 accession AAB34755.1; Glycine Gly m 1 accession ABA54898.1; Glycine Gly m 3 accession CAA11755.1; Glycine Gly m 3 accession 065809.1; Glycine Gly m 3 accession ABU97472.1; Glycine Gly m 4 accession P26987.1; Glycine Gly m 8 2s albumin accession AAD09630.1; Glycine Gly m Bd 28K accession BAB21619.1; Glycine Gly m Bd 28K accession ACD36976.1; Glycine Gly m Bd 28K accession ACD36975.1; Glycine Gly m Bd 28K accession ACD36974.1; Glycine Gly m Bd 28K accession ACD36978.1; Glycine Gly m Bd accession P22895.1; Glycine Gly m Bd accession AAB09252.1; Glycine Gly m Bd accession BAA25899.1; Glycine Glycinin G1 accession CAA26723.1; Glycine Glycinin G1 accession CAA33215.1; Glycine Glycinin G2 accession CAA26575.1; Glycine Glycinin G2 accession CAA33216.1; Glycine Glycinin G3 accession CAA33217.1; Glycine Glycinin G4 accession CAA37044.1; Glycine Glycinin G5 accession AAA33964.1; Glycine Glycinin G5 accession AAA33965.1; Glycine Major Gly 50 kDa allergen accession P82947.1; Glycine Trypsin inhibitor accession AAB23464.1; Glycine Trypsin inhibitor accession AAB23482.1; Glycine Trypsin inhibitor accession AAB23483.1; Glycine Trypsin inhibitor accession CAA56343.1; Glycine Glycinin G4 accession CAA60533.1; Glycine Glycinin G5 accession CAA55977.1.

Some specific allergens of interest include tree nut proteins, which can be provided in a panel of tree nut protein epitopes from one, two, three, four or more different tree nut proteins; in combination with a panel of food allergens; etc. Tree nut allergens include Almonds: Pru du 3/Pru du 3.0101 (123 aa) Accession: ACN11576s/GI:223667948; Pru du 4 Accession: AAL91664/GI:24473798; Pru du 5/Pru du 5.0101 Accession: ABH03379/GI:111013714; Pru du 6/Amandin Accession: ADN39440/GI:307159112; Chain A, Amandin (531 aa)—Accession: 3EHK_A/GI:258588247; Chain B, Amandin (531 aa)—Accession: 3EHK_B/GI: 258588248; Chain C, Amandin (531 aa)—Accession: 3EHK_C/GI:258588249; Prunin 2 precursor/Pru du 6.0201, Accession: ADN39441/GI:307159114; Putative Pru du 6 Accession: AGR27935/GI:523916668. Walnuts: Jug n1 Accession: AAM54365/GI:31321942 or AAB41308/GI: 1794252; Jug n2 Vicillin seed storage protein (481 aa)—Accession: AAM54366/GI:31321944; Jug r1 Albumin Seed Storage, Accession: AAB41308/GI:1794252; Jug r2 Accession: AAF18269/GI:6580762; Jug r3; Jug r4 Accession: AAW29810/GI:56788031. Cashews: Ana o1 accession: AAM73730/GI:21914823; Ana o2 Accession: AAN76862/GI:25991543; Ana o3 Accession: AAL916651/GI: 24473800. Chestnuts: Cas s1 Accession: CAD10374/GI: 16555781; Cas s5 Accession: Q42428/GI:75282355; Chitinase isoform 2 Accession: ADN39439/GI:307159110; Endochitinase Accession: P29137/GI:116301; Cas s8; Cas s9 Accession: CAE46905/GI:46359518. Pecans: Car i1 Accession: AAO32314/GI:28207731; Car i4 Accession: ABW86978/GI:158998780; Accession: ABW86979/GI: 158998782. Hazelnuts: Cor a 1 Accession: CAA50327/GI: 22688; Cor a 1.0102 (161 aa)—Accession: CAA50328/GI: 22690; Cor a 1.0103 (161 aa)—Accession: CAA50325/GI: 22684; Cor a 1.0104 (161 aa)—Accession: CAA50326/GI: 22686; Cor a 1.0201 (161 aa)—Accession: CAA96548/GI: 1321731; Cor a 1.0301 (161 aa)—Accession: CAA96549/GI:1321733; Cor a 1.0401 (161 aa)—Accession: AAD4840/GI:5726304; Cor a 1.0402 (161 aa)—Accession: AAG40329/GI:11762102; Cor a 1.0403 (161 aa)—Accession: AAG40330/GI:11762104; Cor a 1.0404 (161 aa)—Accession: AAG40331/GI:11762106 Cor a 10 Accession: CAC14168/GI:10944737; Cor a 11 Accession: AAL86739/GI:19338630; Cor a 12/oleosin Accession: AAO67349/GI: 49617323; Cor a 13/oleosin Accession: AAO65960/GI: 29170509; Cor a 14/2S albumin Accession: ACO56333/GI: 226437844; Cor a2 Accession: AAK01235/GI:12659206; Cor a8 Accession: AAK28533/GI:13507262; Cor a9 Accession: AAL73404/GI:18479082. Pistachio: Pis v1 Accession: ABG73108/GI:110349081; Pis v2 Accession: ABG73109/GI:110349083; Pis v2.0201/11S globulin precursor ABG73110/GI:110349085, Accession: ABU42022/GI: 156001070; Pis v3; Accession: ABO36677/GI:133711974; Pis v4 Accession: ABR29644/GI:149786150; Pis v5 Accession: ACB55490/GI:171853010.

Some specific allergens of interest include wheat proteins, which can be provided in a panel of wheat protein epitopes from one, two, three, four or more different wheat proteins; in combination with a panel of food allergens; etc. Wheat allergens include Profilin (Tri a 12); Tri a 12.0101 accession P49232; Tri a 12.0102 accession P49233; Tri a 12.0103 accession P49234; Tri a 12.0104 accession B6EF35; Tri a 14.0201 accession D2T2K2; Tri a 15.0101 accession D2TGC3; Tri a 18.0101 accession P10968; Tri a 19.0101; Tri a 21.0101 accession D2T2K3; Tri a 25.0101 accession Q9LDX4; Tri a 26.0101 accession P10388; Tri a 26.0201 accession Q45R38; Tri a 27.0101 accession Q7Y1Z2; Tri a 28.0101 accession Q4W0V7; Tri a 29.0101 accession C7C4X0; Tri a 29.0201 accession D2TGC2; Tri a 30.0101 accession P17314; Tri a 31.0101 accession Q9FS79; Tri a 32.0101 accession Q6W8Q2; Tri a 33.0101 accession Q9ST57; Tri a 34.0101 accession C7C4X1; Tri a 35.0101 accession D2TE72; Tri a 36.0101 accession 335331566; Tri a 37.0101 accession Q9T0P1; Tri a 39.0101 accession J7QW61.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Description of Overall Microfluidic Process Flow

Approximately 100 μL of whole blood is collected from an allergic donor (e.g., to peanut). It is injected into a microfluidic system and split into at least 3 chambers containing either RPMI, anti-IgE, or an allergen (e.g., peanut extract). These stimulations represent a negative control, positive control, and stimulation via allergen, respectively. The stimulation period occurs over a period of 10-30 minutes (at room temperature or 37° C.) followed by washing the cells with 2 mM EDTA in 1× PBS (Ca−/Mg−).

An avidin Alexa488 probe is then injected into each chamber to label basophils that became activated during stimulation. Incubation with the avidin probe for 10-30 minutes is then followed by another wash with a staining buffer (1× PBS, 2 mM EDTA, 0.5% BSA).

The sample is then flown into a region to separate non-basophils and to capture basophils following a series of negative and positive selection steps. We first deplete red blood cells (RBC) via RBC lysis with inertial fractionation or deterministic lateral displacement (DLD). From the resulting WBC sample, basophils are enriched by negative selection by using capture chambers or magnetic beads coated with antibodies (e.g., anti-HLA-DR) that bind to surface markers expressed on non-basophils. The resulting basophil-rich sample is then flowed through a positive selection capture chamber consisting of herringbone structures or pillared arrays that are functionalized with anti-CD123, to select for CD123 expressing cells—a characteristic biomarker for basophils.

Fluorescently labeled activated basophils are counted in each chamber and represented as a percentage of all non-fluorescent cells captured in the anti-CD123 chamber. An individual is said to be allergic to a given allergen if their proportion of basophils activated with the allergen is greater than the basophils activated under the negative control. The expected activation of basophils under the positive control indicates the viability of the test.

Example 2

Component for Microfluidic White Blood Cell Enrichment

1. By Inertial Fractionation

We fractionated blood using an RBC lysis and inertial sorting microfluidic device. We made RBC lysis buffer with 8.29 g of ammonium chloride, 0.037 g EDTA, and 500 mg of potassium bicarbonate in 1 L of ultrapure water. This solution was sterile filtered prior to using. We mixed stimulated and stained blood with RBC lysis buffer at a flow rate ratio of 1:3. The total combined flow rate was such that the blood sample and lysis buffer were allowed ~28 s of lysis time in the incubation channel. For example, our specific geometry called for a 2.03 mL/hr and 6.09 mL/hr flow rates for the blood sample and lysis buffer, respectively. After lysing RBCs the blood sample was quenched to dilute the lysis buffer. Asymmetric serpentine channels were used to focus the blood sample and skim off the buffer solution to achieve and even more diluted the lysis buffer concentration in the sample. The output of this process was then resuspended in ~2 mL of 1× PBS (Ca−/Mg−) and passed through an inertial fractionation spiral at a flow rate necessary to achieve a Dean number of ~6.2 in the spiral. WBCs are collected at the inner outlets (A and B).

2. By Deterministic Lateral Displacement

An alternative method for RBC depletion is by deterministic lateral displacement (DLD). In this method white blood cells are deterministically diverted to one side of a pillared channel based on their size. White blood cells (WBCs) are collected at the outlets indicated in FIG. 4.

Example 3

Capture Chamber Fabrication and Coating

We fabricated microchannels in poly(dimethylsiloxane) (PDMS) using soft lithography. Inlets and outlets of the microchannels were punched using a biopsy puncher (Harris Uni-Core, outer diameter 1.20 mm).

Method I (PDMS/Glass)

1. BSA Immobilization via GA

The cured PDMS (or magnetic beads or glass surface) was rinsed by absolute ethanol and immersed in 10-50% v/v (3-aminopropyl) triethoxysilane (APTES) in absolute ethanol for 10 min at room temperature. Afterwards, it was rinsed by 96% ethanol, followed by air-drying, and then was heat at 80° C. in a vacuum oven for 2 hours to get PDMS-APTES substrate. The PDMS-APTES substrate was activated by 2.5% glutaraldehyde (GA) for 1 hour at room temperature. Then, it was rinsed by pH 8.0 Tris-HCl buffer and dried by argon flow. Bovine serum albumin (BSA) (1 mg/mL in pH 7.4 PBS buffer) was added onto the GA-activated channel and incubated for 2 hours at room temperature, then rinsed by pH 7.4 PBS buffer and followed by air-drying.

2. Antibody Immobilization via Protein A

Figure 5:
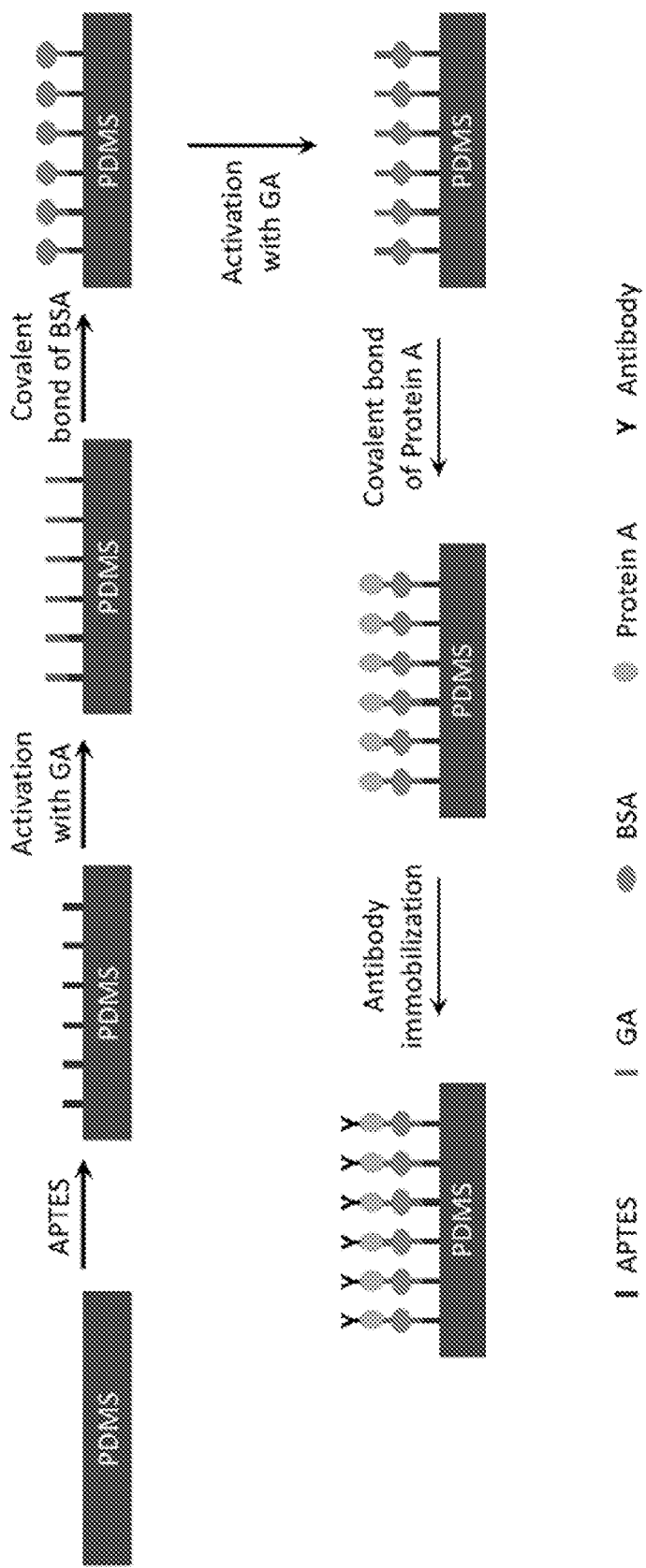
FIG. 5 shows a schematic of the channel coating and functionalization for antibody immobilization with Protein A on a BSA-coated PDMS channel activated with glutaraldehyde (GA).
Figure 6:
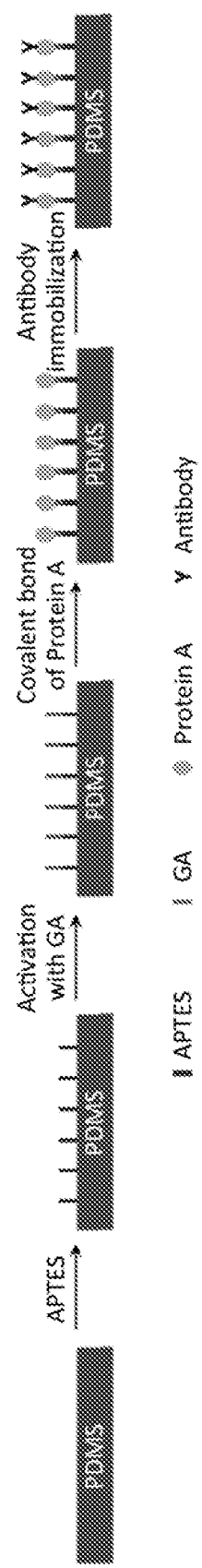
FIG. 6 shows a schematic of the channel coating and functionalization for antibody immobilization with Protein A on a PDMS channel with a glass surface.

The BSA-coated channel was activated with 0.1-2.5% GA for 1 hour at room temperature. Then, protein A (20 μg/ml in pH 7.4 PBS buffer) was added onto the channel and incubated for 1 hour at room temperature for covalently bonding. After rinsed by pH 7.4 PBS buffer, the antibody (5-20 μg/ml in pH 7.4 PBS buffer) was added onto the channel and incubated for 1 hour at room temperature to bind to protein A using the natural affinity of protein A to antibody. Then, the channel was rinsed by pH 7.4 PBS buffer and followed by air-drying. A schematic of the channel coating and functionalization is shown in FIG. 5.

Method II (PDMS/Glass)

1. Protein A Immobilization via GA

The cured PDMS channel (and glass surface) was rinsed by absolute ethanol and immersed in 10-50% v/v (3-aminopropyl) triethoxysilane (APTES) in absolute ethanol for 10 minutes at room temperature. Afterwards, it was rinsed by 96% ethanol, followed by air-drying, and then was heat at 80° C. in a vacuum oven for 2 hours to get PDMS-APTES substrate. The PDMS-APTES substrate was activated by 2.5% glutaraldehyde (GA) for 1 hour at room temperature. Then, it was rinsed by pH 8.0 Tris-HCl buffer and dried by argon flow. Protein A (20 μg/mL in pH 7.4 PBS buffer) was added onto the GA-activated channel and incubated for 2 hours at room temperature, then rinsed by pH 7.4 PBS buffer and followed by air-drying.

2. Antibody Immobilization via Protein A

The antibody (5-20 μg/mL in pH 7.4 PBS buffer) was added onto the channel and incubated for 1 hour at room temperature to bind to protein A using the natural affinity of protein A to antibody. Then, the channel was rinsed by pH 7.4 PBS buffer and followed by air-drying. A schematic of the channel coating and functionalization is shown in the FIG. 6.

Method III (Magnetic Beads)

1. Magnetic Beads Preparation

Dynabeads (Protein A for Immunoprecipitation or Protein G for Immunoprecipitation) were resuspended in the vial and vortexed for >30 sec (or tilted and rotated for 5 min). Then, 50 μL (1.5 mg) Dynabeads were transferred to a tube. The tube containing Dynabeads was put on the magnet to separate beads from the solution. After 5 mins magnetic separation, the supernatant of the solution was removed.

2. Antibody Immobilization

200 μL antibody (5-50 μg/mL in PBS with Tween 20 buffer) were added into the tube containing the separated Dynabeads from last step. Afterwards, the tube was incubated with rotation for 10 min at room temperature to get beads-antibody complex, and then was put on the magnet for 5 mins, followed by supernatant removal. Then, the tube was removed from the magnet and the beads-antibody complex was resuspended in 200 μL PBS with Tween 20. The resuspended beads-antibody complex was washed by gentle pipetting.

Microfluidic Basophil Enrichment

Since basophils are rare (0.5-1% in white blood cells), their isolation and enrichment has been challenging. The identification of basophils in conventional flow cytometry-based basophil activation tests has generally relied on labelling cell-surface markers. But this method requires access to a multi-color flow cytometer which is not readily accessible at the point of care. While commercial basophil enrichment kits exist, the reported percent of basophils captured (i.e., recovery) has had large variability (39%-100%). Enrichment before basophil stimulation separates basophils from blood, and thus from the balance of specific IgE and IgG in the assayed patient that may regulate whether and to what extent basophils undergo activation in vivo.

Basophils can be first activated with allergen in whole blood at 37° C., and then brought to 4° C. for subsequent staining and processing in microfluidics. This sequence of steps ensures basophils are left in their native state during stimulation, and prevents artificial activation in subsequent steps in microfluidics. Basophil enrichment can be performed in a microfluidic device as follows:

1. By Capture Chamber

WBCs are flowed at 1 mL/hr through capture chambers that are functionalized with HLA-DR. The capture chambers consist of structures to increase the incidence of cell contact with functionalized PDMS. The structures are either herringbone structures that induce micro vortices or pillared arrays.

2. By Magnetic Beads

WBCs are tagged with a cocktail of antibodies to negatively select for basophils. The antibody cocktail binds to cells over a period of 5-20 minutes in an incubation channel followed by addition of dextran coated magnetic particles and period of 3-20 minutes for the particles to bind to antibody labeled non-basophilic cells. The sample is then diluted in a 1× PBS solution and inertially focused using asymmetric serpentine channels across a magnetic field. Magnetically tagged non-basophilic cells are diverted to a waste collection and basophils are retained.

What is claimed is:

1. A microfluidic chip component comprising:
   a) an allergen test chamber comprising an allergen;
   b) a first region for separating basophils from other blood cells by negative selection, wherein the first region comprises a plurality of immobilized binding agents capable of selectively binding to one or more cell surface markers on the other blood cells, wherein the cell surface markers are not expressed on basophils;
   c) a first fluidic channel, wherein the first fluidic channel connects the chamber comprising an allergen to the first region;
   d) a second region for capturing basophils by positive selection, wherein the second region comprises a plurality of immobilized binding agents capable of selectively binding to one or more cell surface markers on the basophils and capturing the basophils;
   e) a second fluidic channel, wherein the second fluidic channel connects the first region to the second region; and
   f) a means for detecting basophils activated by the allergen.

2. The microfluidic chip component of claim 1, further comprising a chamber comprising a non-allergenic negative control.

3. The microfluidic chip component of claim 1, further comprising a chamber comprising an anti-immunoglobulin E (IgE) antibody, a protein, or a chemical.

4. The microfluidic chip component of claim 1, wherein the plurality of immobilized binding agents capable of selectively binding to one or more cell surface markers on the other blood cells that are not expressed on basophils comprise at least one antibody selected from the group consisting of an anti-HLA-DR antibody, an anti-CD2 antibody, an anti-CD3 antibody, an anti-CD14 antibody, an anti-CD15 antibody, an anti-CD16 antibody, an anti-CD19 antibody, an anti-CD20 antibody, an anti-CD24 antibody, an anti-CD34 antibody, an anti-CD36 antibody, an anti-CD45RA antibody, an anti-CD56 antibody, an anti-CD66b antibody, and an anti-glycophorin A antibody.

5. The microfluidic chip component of claim 4, wherein the antibody is immobilized on a solid support.

6. The microfluidic chip component of claim 5, wherein the solid support is a magnetic bead, a nonmagnetic bead, a chamber wall, or a fluidic channel wall.

7. The microfluidic chip component of claim 1, wherein the allergen test chamber or the second region further comprises at least one detectably labeled binding agent capable of selectively binding to a basophil activation marker.

8. The microfluidic chip component of claim 7, wherein the at least one detectably labeled binding agent comprises a detectable label selected from the group consisting of a fluorescent label, a chemiluminescent label, and an isotopic label.

9. The microfluidic chip component of claim 7, wherein the at least one detectably labeled binding agent comprises an antibody selected from the group consisting of an anti-CD63 antibody, an anti-CD203 antibody, and an anti-avidin antibody.

10. The microfluidic chip component of claim 1, further comprising a flow-through microfluidic cytometer capable of measuring numbers of activated basophils, wherein the flow-through microfluidic cytometer is fluidically connected to the second region.

11. The microfluidic chip component of claim 1, further comprising a module for depleting red blood cells and platelets.

12. The microfluidic chip component of claim 11, wherein the module for depleting red blood cells and platelets comprises a pillared channel for depleting red blood cells by deterministic lateral displacement (DLD), a red blood cell lysis module, a density gradient for separating the red blood cells and platelets from the white blood cells in the blood sample, a spiral channel to which centrifugal and inertial forces may be applied to separate the red blood cells and platelets from the white blood cells in the blood sample, or a means for applying surface acoustic waves to separate the red blood cells and platelets from the white blood cells in the blood sample.

13. The microfluidic chip component of claim 1, wherein the means for detecting basophils activated by the allergen is a fluorescence detector capable of detecting fluorescence emitted from the captured basophils within the second region, or a sensor capable of detecting increases in electrochemical current.

14. The microfluidic chip component of claim 1, further comprising electrical means for measuring resistivity, impedance, or conductance of the basophils.

15. The microfluidic chip component of claim 1, wherein the microfluidic chip component comprises:
   a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel;
b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a wash buffer for removing unbound agents, wherein the chamber comprising the wash buffer for removing unbound binding agents is fluidically connected to the chamber for incubating activated basophils with detectably labeled binding agents, iii) a channel connecting the chamber for incubating activated basophils with detectably labeled binding agents and the chamber comprising the wash buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the wash buffer for removing unbound binding agents and v) a second waste outlet, wherein the second waste channel is fluidically connected to the second asymmetric serpentine inertial focusing channel;
c) a third portion for lysing red blood cells comprising: i) a chamber comprising a lysis buffer, wherein the chamber comprising the lysis buffer is fluidically connected to the second asymmetric serpentine inertial focusing channel, ii) a chamber comprising a washing buffer, iii) a channel connecting the chamber comprising the lysis buffer and the chamber comprising the washing buffer, iv) a third asymmetric serpentine inertial focusing channel, wherein the third asymmetric serpentine inertial focusing channel is fluidically connected to the channel connecting the chamber comprising the lysis buffer and the chamber comprising the washing buffer, v) a third waste outlet, wherein the third waste outlet is fluidically connected to the third asymmetric serpentine inertial focusing channel;
d) a fourth portion for sample fractionation comprising i) an inertial fractionation spiral and ii) a fourth waste outlet, wherein the fourth waste outlet is fluidically connected to the inertial fractionation spiral; and
e) a fifth portion for capturing basophils comprising i) a basophil negative selection chamber, ii) a basophil positive selection chamber, wherein the basophil positive selection chamber is fluidically connected to the basophil negative selection chamber, iii) a chamber comprising a wash buffer, wherein the chamber comprising the wash buffer is fluidically connected to the basophil positive selection chamber, and iv) an exit channel, wherein the exit channel is fluidically connected to the basophil positive selection chamber.

16. A method of using the microfluidic chip component of claim 15, the method comprising:
a) introducing the blood sample into the first inlet;
b) introducing the allergen into the second inlet;
c) flowing the blood sample and the allergen into the incubation channel, wherein basophils in the blood sample are exposed to the allergen for a time sufficient to allow activation of any basophil comprising an immunoglobulin E (IgE) specific for the allergen that is bound at an $F_c\varepsilon RI$ receptor;
d) flowing the blood sample through the first asymmetric serpentine inertial focusing channel to the chamber for incubating activated basophils with detectably labeled binding agents, wherein contacting the activated basophils with said detectably labeled binding agents in said chamber results in said binding agents selectively binding to at least one activation marker on the activated basophils;
e) removing the detectably labeled binding agents that have not bound to the activated basophils at said at least one activation marker by washing the basophils with the washing buffer;
f) flowing the blood sample through the second asymmetric serpentine inertial focusing channel to the chamber for lysing red blood cells, wherein contacting the red blood cells in the blood sample with the lysis buffer lyses the red blood cells;
g) flowing the blood sample through the third asymmetric serpentine inertial focusing channel to the inertial fractionation spiral, wherein red blood cells are separated from the basophils in the blood sample;
h) depleting the blood sample of the red blood cells by expelling the red blood cells out of the fourth waste outlet;
i) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and
j) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils.

17. The microfluidic chip component of claim 1, wherein the microfluidic chip component comprises:
a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel;
b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel;

c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells, wherein the third waste outlet is fluidically connected to the DLD array; and d) a fourth portion for capturing basophils comprising i) a basophil negative selection chamber, ii) a basophil positive selection chamber, wherein the basophil positive selection chamber is fluidically connected to the basophil negative selection chamber, iii) a chamber comprising a washing buffer, wherein the chamber comprising the washing buffer is fluidically connected to the basophil positive selection chamber, and iv) an exit channel, wherein the exit channel is fluidically connected to the basophil positive selection chamber.

18. A method of using the microfluidic chip component of claim 17, the method comprising:

a) introducing the blood sample into the first inlet;
b) introducing the allergen into the second inlet;
c) flowing the blood sample and the allergen into the incubation channel, wherein basophils in the blood sample are exposed to the allergen for a time sufficient to allow activation of any basophil comprising an immunoglobulin E (IgE) specific for the allergen that is bound at an $F_c\varepsilon RI$ receptor;
d) flowing the blood sample through the first asymmetric serpentine inertial focusing channel to the chamber for incubating activated basophils with detectably labeled binding agents, wherein contacting the activated basophils with said detectably labeled binding agents in said chamber results in said binding agents selectively binding to at least one activation marker on the activated basophils;
e) removing the detectably labeled binding agents that have not bound to the activated basophils at said at least one activation marker by washing the basophils with the washing buffer;
f) flowing the blood sample through the second asymmetric serpentine inertial focusing channel;
g) flowing the blood sample through the DLD array, wherein the red blood cells are separated from the basophils in the blood sample;
h) depleting the blood sample of the red blood cells by expelling the red blood cells out of the third waste outlet;
i) flowing the remaining blood sample to the basophil negative selection chamber, wherein the blood cells other than the basophils are captured by contacting the blood cells with the plurality of immobilized binding agents in the basophil negative selection chamber, wherein said binding agents selectively bind to one or more cell surface markers on the blood cells other than the basophils that are not expressed on the basophils; and
j) flowing the blood sample to the basophil positive selection chamber, wherein the basophils are captured by contacting the basophils with the plurality of immobilized binding agents in the basophil positive selection chamber, wherein said binding agents selectively bind to one or more cell surface markers on the basophils.

19. The microfluidic chip component of claim 1, wherein the microfluidic chip component comprises:

a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel;

b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel;

c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells, wherein the third waste outlet is fluidically connected to the DLD array; and d) a fourth portion for compartmentalizing the DLD array product into discrete volumes, wherein the fourth portion comprises a plurality of compartments, said compartments comprising fluidic or solid state chambers to contain cells.

20. The microfluidic chip component of claim 1, wherein the microfluidic chip component comprises:

a) a first portion for stimulating basophils comprising: i) a first inlet for loading a blood sample, ii) a second inlet for loading an allergen, iii) an incubation channel for stimulating the basophils in the blood sample with the allergen, wherein the first and second inlets are fluidically connected to the incubation channel, iv) a chamber comprising a washing buffer, wherein the chamber comprising the washing buffer is fluidically connected to the incubation channel, v) a first asymmetric serpentine inertial focusing channel, wherein the first asymmetric serpentine inertial focusing channel is fluidically connected to the incubation channel, and vi) a first waste outlet, wherein the first waste outlet is fluidically connected to the asymmetric serpentine inertial focusing channel;

b) a second portion for labeling activated basophils comprising: i) a chamber for incubating activated basophils with detectably labeled binding agents that selectively bind to at least one activation marker on the basophils, wherein the chamber for incubating activated basophils with detectably labeled binding agents is fluidically connected to the first asymmetric serpentine inertial focusing channel, ii) a chamber comprising a washing buffer for removing unbound binding agents, iii) a channel connecting the chamber for incubating activated basophils with detectably labeled binding agents and the chamber comprising a washing buffer for removing unbound binding agents, iv) a second asymmetric serpentine inertial focusing channel, wherein the second asymmetric serpentine inertial focusing channel is fluidically connected to the channel connecting the chamber for incubating activated basophils with detectably labeled binding agents and the chamber comprising the washing buffer for removing unbound binding agents and v) a second waste outlet, wherein the second waste outlet is fluidically connected to the second asymmetric serpentine inertial focusing channel;

c) a third portion for sample fractionation comprising: i) a DLD array, wherein the DLD array is fluidically connected to the second asymmetric serpentine inertial focusing channel, ii) a chamber comprising a running buffer, wherein the chamber comprising the running buffer is fluidically connected to the DLD array, and ii) a third waste outlet for expelling red blood cells, wherein the third waste outlet is fluidically connected to the DLD array; and d) a fourth portion for basophil isolation comprising: i) an incubation chamber for binding antibodies specific for non-basophils to non-basophils, ii) a flow channel for removing the non-basophils such that a basophil isolation product exits the flow channel; and e) a fifth portion for compartmentalizing the basophil isolation product into discrete volumes, wherein the fifth portion comprises a plurality of compartments, said compartments comprising fluidic or solid state chambers to contain cells.

21. The microfluidic chip component of claim 1, wherein the microfluidic chip component comprises:

a) a first portion for compartmentalizing whole blood into discrete volumes, wherein the first portion comprises a plurality of compartments, said compartments comprising fluidic or solid state chambers to contain cells;

b) a second portion for stimulating whole blood comprising: i) an inlet for loading an allergen, iii) an incubation channel for stimulating the basophils in the blood sample with the allergen, wherein the compartments of a) and the allergen inlet are fluidically connected to the incubation channel;

c) a third portion for adding reagents to compartments containing activated basophils comprising: i) an inlet for adding reagents to detect activated basophils, ii) an incubation channel, wherein the compartments and the inlet for adding reagents to detect activated basophils are fluidically connected to the incubation channel; and d) a fourth portion for detecting a measurable signal for the activated basophils that are detected by the reagents.

\* \* \* \* \*

UNITED STATES PATENT AND TRADEMARK OFFICE
CERTIFICATE OF CORRECTION

PATENT NO. : 12,239,982 B2  
APPLICATION NO. : 17/292782  
DATED : March 4, 2025  
INVENTOR(S) : Sindy K. Y. Tang et al.

Page 1 of 1

It is certified that error appears in the above-identified patent and that said Letters Patent is hereby corrected as shown below:

On the Title Page

In item (71), delete "Sindy K. Y. Tang, Palo Alto, CA (US); Kari C. Nadeau, Los Altos Hills, CA (US); Bryan J. Bunning, San Mateo, CA (US); Nicolas Castano, Stanford, CA (US); Fengjiao Lyu, Stanford, CA (US); Seth Cordts, Palo Alto, CA (US);"

In item (72), Please correct the first inventor to read: --Sindy K. Y. Tang, Stanford, CA (US)--

Signed and Sealed this  
Twenty-seventh Day of May, 2025

Coke Morgan Stewart  
*Acting Director of the United States Patent and Trademark Office*